US011229643B2

(12) United States Patent
Fairhurst et al.

(10) Patent No.: US 11,229,643 B2
(45) Date of Patent: Jan. 25, 2022

(54) COMBINATIONS OF FGFR4 INHIBITORS AND BILE ACID SEQUESTRANTS

(71) Applicant: NOVARTIS AG, Basel (CH)

(72) Inventors: Robin Alec Fairhurst, Basel (CH); Diana Graus Porta, Basel (CH); Jacqueline Kinyamu-Akunda, East Hanover, NJ (US); Andreas Joerg Mahl, Basel (CH); Luigi Manenti, Basel (CH); Andreas Weiss, Basel (CH); Armin Wolf, Basel (CH); Kuno Wuersch, Basel (CH)

(73) Assignee: NOVARTIS AG, Basel (CH)

( * ) Notice: Subject to any disclaimer, the term of this patent is extended or adjusted under 35 U.S.C. 154(b) by 142 days.

(21) Appl. No.: 16/347,194

(22) PCT Filed: Nov. 1, 2017

(86) PCT No.: PCT/IB2017/056787
§ 371 (c)(1),
(2) Date: May 2, 2019

(87) PCT Pub. No.: WO2018/083603
PCT Pub. Date: May 11, 2018

(65) Prior Publication Data
US 2020/0261444 A1    Aug. 20, 2020

Related U.S. Application Data

(60) Provisional application No. 62/416,222, filed on Nov. 2, 2016.

(51) Int. Cl.
*A61K 31/496* (2006.01)
*A61K 31/14* (2006.01)

(52) U.S. Cl.
CPC ............ *A61K 31/496* (2013.01); *A61K 31/14* (2013.01)

(58) Field of Classification Search
CPC .............. A61K 31/496; A61K 31/506; A61K 2300/00; A61K 31/14; A61K 31/4545; A61K 31/785; A61P 35/00
See application file for complete search history.

(56) References Cited

U.S. PATENT DOCUMENTS

2009/0110655 A1    4/2009  Hashimoto et al.

FOREIGN PATENT DOCUMENTS

| CN | 105008548 A | 10/2015 | | |
|---|---|---|---|---|
| JP | 2009120597 A | 6/2009 | | |
| JP | 2012531415 A | 12/2012 | | |
| JP | 2014524444 A | 9/2014 | | |
| WO | 2010151439 A1 | 12/2010 | | |
| WO | 2013025969 A1 | 2/2013 | | |
| WO | 2015195509 A2 | 12/2015 | | |
| WO | 2016054483 A1 | 4/2016 | | |
| WO | WO-2016054483 A1 | * | 4/2016 | ............ A61K 31/55 |
| WO | 2016151501 A1 | 9/2016 | | |
| WO | WO-2016184909 A1 | * | 11/2016 | ............... A61P 3/04 |

OTHER PUBLICATIONS

Scaldaferri et al. (Intern Emerg Med 2013, 8, 205-210). (Year: 2013).*
Staels (Curr Diab Rep 2010, 10, 70-77). (Year: 2010).*
University of Massachusetts (Therapeutic Class Overview Bile Acid Sequestrants, 2013, p. 1-4). (Year: 2013).*
Howard R. Mellor, "Targeted inhibition of the FGF19-FGFR4 pathway in hepatocellular carcinoma; translational safety considerations", Liver International, vol. 34, No. 6, Jul. 1, 2014, p. e1-e9.
Dimitra Repana et al, "Targeting FGF19/FGFR4 Pathway: A Novel Therapeutic Strategy for Hepatocellular Carcinoma", Diseases, vol. 3, No. 4, Oct. 28, 2015, p. 294-305.
Pai, R. et al., "Antibody-mediated inhibition of fibroblast growth factor 19 results in increased bile acids synthesis and ileal malabsorption of bile acids in cynomolgus monkeys", Toxicological Sciences, 2012, vol. 126, No. 2, pp. 446-456.
Kanki et al., "Usefulness and problems of blood micro RNA-122 as a biomarker for hepatic impairment", Pharmacia, 2015, vol. 51, No. 3, p. 257.

* cited by examiner

*Primary Examiner* — Umamaheswari Ramachandran
(74) *Attorney, Agent, or Firm* — Rimôn, P.C.

(57) ABSTRACT

The present invention relates to a pharmaceutical combination comprising an FGFR4 inhibitor and a bile acid sequestrant, to the use of the pharmaceutical combination in the treatment of cancer, to the use of a bile acid sequestrant to reduce or mitigate side-effects associated with FGFR4 inhibition therapy.

12 Claims, 2 Drawing Sheets

COMBINATIONS OF FGFR4 INHIBITORS AND BILE ACID SEQUESTRANTS

FIELD OF THE INVENTION

The present invention relates to a pharmaceutical combination comprising an FGFR4 inhibitor, particularly a selective FGFR4 inhibitor, and a bile acid sequestrant, to the use of said pharmaceutical combination in the treatment of cancer and to the use of a bile acid sequestrant for reducing or preventing side effects, in particular liver enzyme elevation, during treatment with an FGFR4 inhibitor.

BACKGROUND OF THE INVENTION

There have been recent advances in the treatment of certain cancers, notably cancers associated with the FGFR4 pathway. For instance, WO2015059668 and WO2014/011900 describe FGFR4 inhibitors which can be used in the treatment of cancer, in particular liver cancer.

Liver cancer includes hepatocellular carcinoma (HCC) which is the fifth most common form of cancer worldwide and the second most common cause of cancer-related deaths. Potentially curative therapies, such as surgical resection, liver transplant or other local treatments, result in survival rates of between 50-70% at 5 years for patients with early stage HCC. However, despite advances in diagnostic techniques and increased surveillance, the majority of HCC cases present with advanced, inoperable tumors. Sorafenib is the only approved drug in HCC with marginal improvement in overall survival (OS) and poor tolerability.

There is thus a need to provide therapies for cancer, including therapies for HCC, which have one or more of the following benefits: improved safety profiles, improved toxicity profiles, improved efficacy compared to a standard of care, tolerability by patients, advantages to patients in terms of overall response rate, overall survival, time to progression.

As is the case for the treatment of any cancer, it is incumbent to the pharmaceutical industry to also provide ways of mitigating or reducing side effects associated with cancer treatment, e.g. treatment of HCC. There still remains a need to provide solutions for managing side effects in a way which is optimal for the patients receiving treatment, specially for patients suffering from HCC.

SUMMARY OF THE INVENTION

The present inventors have found that a bile acid sequestrant such as cholestyramine mitigates and reverses side effects such as increases in alanine aminotransferase (ALT) levels observed after administration of a selective FGFR inhibitor.

The present invention thus addresses some of the needs described above by providing a pharmaceutical combination comprising an FGFR4 inhibitor, particularly a selective FGFR4 inhibitor, and a bile acid sequestrant.

In another aspect, the present invention relates to a pharmaceutical combination comprising an FGFR4 inhibitor, preferably a selective FGFR4 inhibitor, and a bile acid sequestrant for use as a medicament.

In another aspect, the present invention relates to a pharmaceutical combination comprising an FGFR4 inhibitor, preferably a selective FGFR4 inhibitor, and a bile acid sequestrant for use in the treatment of cancer, in particular liver cancer.

In a further aspect, the invention relates to the use of a bile acid sequestrant for reducing or preventing side effects associated with FGFR4 inhibition therapy. The FGFR inhibition therapy includes administration of an FGFR4 inhibitor, preferably Compound A, or a pharmaceutically acceptable salt, e.g. a citrate salt, thereof.

In a further aspect, the invention relates to the use of a bile acid sequestrant for reducing or preventing side effects associated with FGFR4 inhibition therapy, wherein the side effect does not include diarrhea.

In another aspect, the invention relates to a method for diminishing the incidence or severity of side effects associated with FGFR4 inhibition therapy comprising administering to a subject in need of FGFR4 inhibition therapy a combination comprising a therapeutically effective amount of a bile acid sequestrant and a therapeutically effective amount of an FGFR4 inhibitor, preferably a selective FGFR4 inhibitor In still another aspect, the invention relates to a therapeutic regimen comprising the simultaneous or sequential administration of a bile acid sequestrant and an FGFR4 inhibitor.

DETAILED DESCRIPTION OF THE INVENTION

Figure 1:
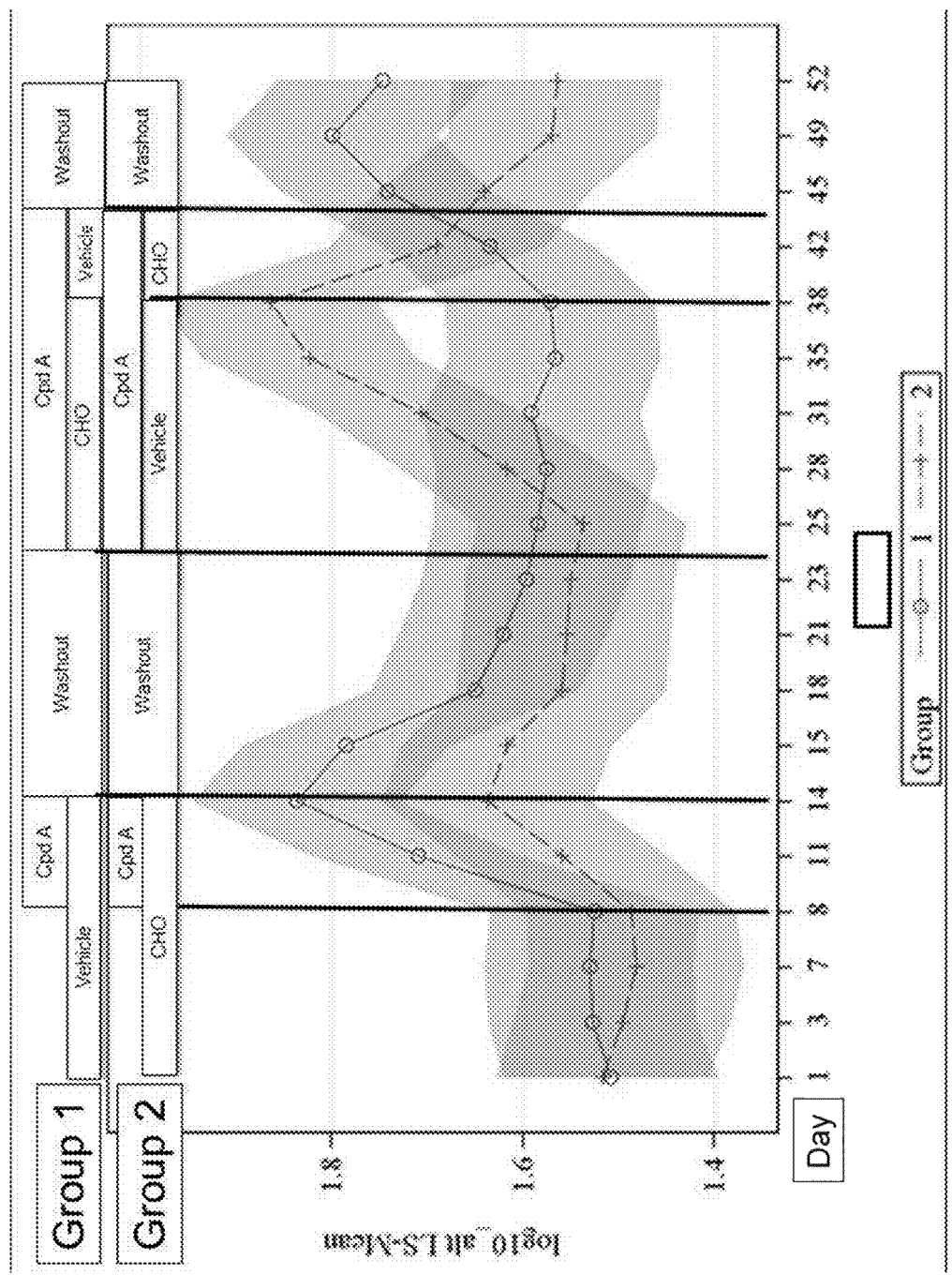
FIG. 1 shows the variation of ALT (alanine aminotransferase) level in the serum of dogs receiving an FGFR4 inhibitor (N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide, Compound A, abbreviated as Cpd A) concurrently or sequentially with a bile acid sequestrant (cholestyramine, abbreviated as CHO).

The present invention relates to a pharmaceutical combination comprising an FGFR4 inhibitor, preferably a selective FGFR4 inhibitor, and a bile acid sequestrant.

In the present description, a "pharmaceutical combination" refers to a non-fixed combination. The term "non-fixed combination" means that the active ingredients, e.g. an FGFR4 inhibitor (or a selective FGFR4 inhibitor) and a bile acid sequestrant, are both administered to a patient as separate entities either simultaneously or sequentially with no specific time limits, wherein such administration provides therapeutically effective levels of the two compounds in the body of the patient.

In the following, a "pharmaceutical combination of the invention" refers to a pharmaceutical combination comprising an FGFR4 inhibitor, preferably a selective FGFR4 inhibitor, and a bile acid sequestrant. In a specific embodiment, the pharmaceutical combination of the invention refers to N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide, optionally in citric acid salt form, and cholestyramine.

As used herein, the term "active ingredient" refers independently to each combination partner, namely the FGFR4 inhibitor and the bile acid sequestrant.

As used herein, the term "FGFR4" refers to fibroblast growth factor receptor 4, also known as CD334, JTK2, TKF.

FGFR4 inhibition therapy refers to a therapy comprising the use of an FGFR4 inhibitor. In an embodiment, the FGFR4 inhibition therapy is for the treatment of cancer. Preferably, the FGFR4 inhibition therapy is for the treatment of liver cancer, including HCC.

As used herein, an FGFR4 inhibitor is a compound which inhibits FGFR4. Preferably, the FRFR4 inhibitor is a selective FGFR4 inhibitor and, for example, is a compound that inhibits FGFR4 selectively compared to FGFR1, FGFR2 and FGFR3. FGFR4 inhibitors may be small molecules or large molecules. The FGFR4 inhibitors of the present invention are preferably small molecules.

Therapies involving FGFR4 blocking antibodies have been described for instance in the following patent applications WO2009/009173, WO2007/136893, WO2012/138975, WO2010/026291, WO2008/052798, WO2010/004204, WO2014/105849, WO2014/165287 and WO2016/023894. WO2014/144737, WO2014/145909, WO2014/011900, WO2015/057963, WO2015/057938, WO2015/030021, WO2015/107171, WO2015/059668, WO2016/064960, WO2016/134320, WO2016/134314, WO2016/134294 also describe low molecular weight FGFR4 inhibitors.

In an embodiment, the FGFR4 inhibitor used in the combination of the invention is any of the FGFR4 inhibitors described in any of patent applications WO2009/009173, WO2007/136893, WO2012/138975, WO2010/026291, WO2008/052798, WO2010/004204, WO2014/105849, WO2014/165287, WO2016/023894, WO2014/144737, WO2014/145909, WO2014/011900, WO2015/057963, WO2015/057938, WO2015/030021, WO2015/107171, WO2015/059668, WO2016/064960, WO2016/134320, WO2016/134314, and WO2016/134294.

In an embodiment, the FGFR4 inhibitor used in the combination of the invention is any of the FGFR4 inhibitors described in WO2014/144737, WO2014/145909, WO2014/011900, WO2015/057963, WO2015/057938, WO2015/030021, WO2015/107171, WO2015/059668, WO2016/064960, WO2016/134320, WO2016/134314, WO2016/134294, in free form or in pharmaceutically acceptable salt form.

In an embodiment, the FGFR4 inhibitor used in the combination of the invention is a compound as defined in WO2015059668, in free form or in pharmaceutically acceptable salt form.

Therefore, in one embodiment, the FGFR4 inhibitor used in the pharmaceutical combination of the invention is a compound of formula (I) in free form or in pharmaceutically acceptable salt form

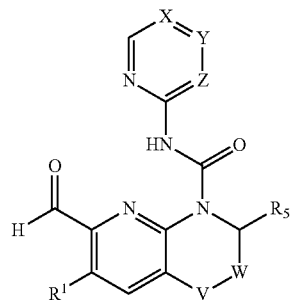

(I)

wherein
V is selected from $CH_2$, O, CH(OH);
W is selected from $CH_2$, $CH_2CH_2$, bond;
X is $C(R^X)$ or N;
Y is $C(R^Y)$ or N;
Z is CH or N;
wherein when X is N, Y and Z are not N;
wherein when Y is N, X and Z are not N;
wherein when Z is N, X and Y are not N;
$R^X$ is selected from hydrogen, halogen, halo$C_1$-$C_3$alkyl, cyano, $C_1$-$C_6$alkyl, hydroxy$C_1$-$C_6$alkyl;
$R^Y$ is selected from hydrogen, halogen, $C_1$-$C_3$alkyl, $C_1$-$C_6$alkoxy, hydroxy$C_1$-$C_3$alkoxy, $NR^{Y1}R^{Y2}$, cyano, $C_1$-$C_3$alkoxy$C_1$-$C_3$alkoxy, $C_1$-$C_3$alkoxy-halo$C_1$-$C_3$alkoxy, di($C_1$-$C_3$alkyl)amino$C_1$-$C_6$alkoxy, O—$(CH_2)_{0-1}$—$R^{Y3}$, $CR^{Y6}R^{Y7}$, S—$C_1$-$C_3$alkyl, halo$C_1$-$C_6$alkoxy optionally substituted with hydroxy;
or
$R^X$ and $R^Y$ together with the ring to which they are attached form a bicyclic aromatic ring system optionally further comprising one or two heteroatoms selected from N, O, or S, which ring system is optionally substituted with $C_1$-$C_3$alkyl;
$R^{Y1}$ is hydrogen and
$R^{Y2}$ is selected from $C_1$-$C_6$alkyl; hydroxy$C_1$-$C_6$alkyl; halo$C_1$-$C_6$alkyl optionally substituted with hydroxy; $C_1$-$C_4$alkoxy$C_1$-$C_6$alkyl; halo$C_1$-$C_3$alkoxy$C_1$-$C_6$alkyl; $(CH_2)_{0-1}$—$R^{Y4}$; di($C_1$-$C_3$alkyl)amino$C_1$-$C_6$alkyl substituted with hydroxy; bicyclo$C_5$-$C_8$alkyl optionally substituted with hydroxy$C_1$-$C_3$alkyl; phenyl substituted with $S(O)_2$—$CH(CH_3)_2$; $C_2$-$C_3$alkylsulfonic acid;
or
$R^{Y1}$ and $R^{Y2}$ together with the N atom to which they are attached form a saturated or unsaturated non-aromatic 6-membered heterocyclic ring which may contain an O atom, which ring may be substituted once or twice by $R^{Y5}$;
$R^{Y3}$ is selected from quinuclidinyl, a 4-, 5- or 6-membered saturated heterocyclic ring comprising at least one heteroatom selected from N, O or S, or a 5- or 6-membered aromatic heterocyclic ring, which saturated or aromatic heterocyclic ring is optionally substituted with $C_1$-$C_3$alkyl and/or oxo;
$R^{Y4}$ is a 4-, 5- or 6-membered saturated heterocyclic ring comprising at least one heteroatom selected from N, O, or S, which ring is optionally substituted with $C_1$-$C_3$alkyl;
$R^{Y5}$ is independently selected from $C_1$-$C_3$alkyl, hydroxy, di($C_1$-$C_3$alkyl)amino$C_1$-$C_3$alkyl,
or
two $R^{Y5}$ attached at the same carbon atom form together with the carbon atom to which they are attached a 5-membered saturated heterocyclic ring comprising at least one heteroatom selected from N, O or S, which ring is substituted once or more than once with $C_1$-$C_3$alkyl;
$R^{Y6}$ and $R^{Y7}$ together with the carbon atom to which they are attached form a 6-membered saturated or unsaturated non-aromatic heterocyclic ring comprising one heteroatom selected from N, O or S;
$R^1$ is selected from hydrogen; halogen; $C_1$-$C_3$alkyl; halo$C_1$-$C_3$alkyl; hydroxy$C_1$-$C_3$alkyl; $C_3$-$C_6$cycloalkyl; $CH_2NR^2R^3$; $CH(CH_3)NR^2R^3$; $C_1$-$C_3$alkoxy$C_1$-$C_3$alkyl; $CH_2CO_2H$; C(O)H; $C_1$-$C_3$alkoxy; a 5- or 6-membered saturated heterocyclic or aromatic heterocyclic ring comprising at least one heteroatom selected from N, O or S, which ring is optionally substituted once or more than once with a group independently selected from $C_1$-$C_3$alkyl, halo$C_1$-$C_3$alkyl, oxetanyl or oxo;

$R^2$ is selected from $C_1$-$C_3$alkyl, di($C_1$-$C_3$alkyl)amino$C_1$-$C_3$alkyl;

$R^3$ is selected from $C_1$-$C_3$alkyl, C(O)$C_1$-$C_3$alkyl, C(O)—$CH_2$—OH, C(O)—$CH_2$—O—$CH_3$, C(O)—$CH_2$—N($CH_3$)$_2$, S(O)$_2CH_3$;

or $R^2$ and $R^3$ together with the N atom to which they are attached form a saturated 5- or 6-membered ring optionally comprising one additional heteroatom selected from N, N-oxide, O or S, which ring may be substituted once or more than once with $R^4$;

$R^4$ is independently selected from $C_1$-$C_3$alkyl, di($C_1$-$C_3$alkyl)amino, C(O)$CH_3$, hydroxy;

or two $R^4$ attached at the same carbon atom form together with the carbon atom to which they are attached a 4-, 5- or 6-membered non-aromatic heterocyclic ring comprising at least one heteroatom selected from N, O or S;

or two $R^4$ attached at the same ring atom form an oxo group;

$R^5$ is selected from hydrogen or $C_1$-$C_3$alkyl.

As used herein, the term "$C_1$-$C_6$alkyl" refers to a straight or branched hydrocarbon chain radical consisting solely of carbon and hydrogen atoms, containing no unsaturation, having from one to six carbon atoms, and which is attached to the rest of the molecule by a single bond. The term "$C_1$-$C_4$alkyl" is to be construed accordingly. The term "$C_1$-$C_3$alkyl" is to be construed accordingly. Examples of $C_1$-$C_6$alkyl include, but are not limited to, methyl, ethyl, n-propyl, 1-methylethyl (iso-propyl), n-butyl, n-pentyl and 1,1-dimethylethyl (t-butyl).

As used herein, the term "hydroxy$C_1$-$C_6$alkyl" refers to a radical of formula $R_a$—OH, wherein $R_a$ is $C_{1-6}$alkyl as defined above. Examples of hydroxy$C_1$-$C_6$alkyl include, but are not limited to, hydroxy-methyl, 2-hydroxy-ethyl, 2-hydroxy-propyl, 3-hydroxy-propyl and 5-hydroxypentyl.

As used herein, the term "$C_3$-$C_6$cycloalkyl" refers to saturated monocyclic hydrocarbon groups of 3-6 carbon atoms. Examples of $C_3$-$C_6$cycloalkyl include cyclopropyl, cyclobutyl, cyclopentyl and cyclohexyl.

As used herein, the term "$C_1$-$C_6$alkoxy" refers to a radical of the formula —$OR_a$ where $R_a$ is a $C_1$-$C_6$alkyl radical as generally defined above. The term "$C_1$-$C_3$alkoxy" is to be construed accordingly. Examples of $C_1$-$C_6$alkoxy include, but are not limited to, methoxy, ethoxy, propoxy, iso-propoxy, butoxy, isobutoxy, pentoxy, and hexoxy.

As used herein, the term "$C_1$-$C_4$alkoxy$C_1$-$C_6$alkyl" refers to a radical of the formula $R_b$—O—$R_a$ where $R_a$ is a $C_1$-$C_4$alkyl radical and $R_b$ is a $C_1$-$C_6$alkyl radical as defined above. The term "$C_1$-$C_3$alkoxy$C_1$-$C_6$alkyl" is to be construed accordingly. The oxygen atom may be bonded to any carbon atom in either alkyl radical. Examples of $C_1$-$C_4$alkoxy$C_1$-$C_6$alkyl include, but are not limited to, methoxy-methyl, methoxy-ethyl, ethoxy-ethyl, 1-ethoxy-propyl and 2-methoxy-butyl.

"Halogen" or "halo" refers to bromo, chloro, fluoro or iodo.

As used herein, the term "halogen$C_1$-$C_6$alkyl" or "halo$C_1$-$C_6$alkyl" refers to $C_1$-$C_6$alkyl radical, as defined above, substituted by one or more halo radicals, as defined above. Examples of halogen$C_1$-$C_6$alkyl include, but are not limited to, trifluoromethyl, difluoromethyl, fluoromethyl, trichloromethyl, 2,2,2-trifluoroethyl, 1-fluoromethyl-2-fluoroethyl, 3-bromo-2-fluoropropyl and 1-bromomethyl-2-bromoethyl.

As used herein, the term "halo$C_1$-$C_3$alkoxy" refers to $C_1$-$C_3$alkoxy as defined above, substituted by one or more halo radicals, as defined above. Examples of halo$C_1$-$C_3$alkoxy include, but are not limited to, trifluoromethoxy, difluoromethoxy, trifluoroethoxy.

As used herein, the term "hydroxy$C_1$-$C_3$alkoxy" refers to a $C_1$-$C_3$alkoxy radical as defined above, wherein one of the hydrogen atoms of the $C_1$-$C_3$alkoxy radical is replaced by OH. Examples of hydroxy$C_1$-$C_3$alkoxy include, but are not limited to, hydroxymethoxy, hydroxyethoxy.

As used herein, the term "$C_1$-$C_3$alkoxy$C_1$-$C_3$alkoxy" refers to a $C_1$-$C_3$alkoxy radical as defined above, wherein one of the hydrogen atoms of the $C_{1-3}$alkoxy radical is replaced by —O—$C_1$-$C_3$alkyl. Examples of $C_1$-$C_3$alkoxy$C_1$-$C_3$alkoxy include, but are not limited to, methoxymethoxy, ethoxymethoxy.

As used herein, the term "$C_1$-$C_3$alkoxy-halo$C_1$-$C_3$alkoxy" refers to a halo$C_1$-$C_3$alkoxy radical as defined above, wherein one of the hydrogen atoms of the halo$C_1$-$C_3$alkoxy radical is replaced by —O—$C_1$-$C_3$alkyl. Examples of $C_1$-$C_3$alkoxy-halo$C_1$-$C_3$alkoxy include, but are not limited to, methoxytrifluoropropyloxy.

As used herein, the term "di($C_1$-$C_3$alkyl)amino$C_1$-$C_6$alkyl" refers to a radical of the formula —$R_{a1}$—N($R_{a2}$)—$R_{a2}$ where $R_{a1}$ is a $C_1$-$C_6$alkyl radical as defined above and each $R_{a2}$ is a $C_1$-$C_3$alkyl radical, which may be the same or different, as defined above. The nitrogen atom may be bonded to any carbon atom in any alkyl radical. As described herein, the "di$C_1$-$C_3$alkylamino$C_1$-$C_6$alkyl" may be substituted with hydroxy.

As used herein, the term "di($C_1$-$C_3$alkyl)amino$C_1$-$C_6$alkoxy" refers to a radical of the formula —$R_{a1}$—N($R_{a2}$)—$R_{a2}$ where $R_{a1}$ is a $C_1$-$C_6$alkoxy radical as defined above and each $R_{a2}$ is a $C_1$-$C_3$alkyl radical, which may be the same or different, as defined above.

As used herein, the term "6-membered saturated heterocyclic ring comprising one heteroatom selected from N, O or S" includes piperidyl, tetrahydropyranyl and tetrahydrothiopyranyl.

As used herein, the term "6-membered unsaturated non-aromatic heterocyclic ring comprising one heteroatom selected from N, O or S" includes, but is not limited to, tetrahydropyridinyl, dihydropyranyl, dihydrothiopyranyl.

As used herein, the term "a 4-, 5-, or 6-membered saturated heterocyclic ring comprising at least one heteroatom selected from N, O or S" includes as examples, but is not limited to, azetidinyl, oxetanyl, pyrrolidyl, tetrahydrofuryl, tetrahydrothienyl, piperidyl, piperazinyl, tetrahydropyranyl, morpholinyl.

As used herein, the term "5-membered saturated heterocyclic ring" includes as example, but is not limited to, pyrrolidine.

As used herein, the term "a saturated 5- or 6-membered ring optionally comprising one additional heteroatom selected from N, O or S" in relation to the embodiments where $R^2$ and $R^3$ together with the N atom to which they are attached form said ring, includes as examples, but is not limited to, pyrrolidine, oxazolidine, piperazine, morpholine, thiomorpholine rings.

As used herein, the term a "4-, 5- or 6-membered non-aromatic heterocyclic ring comprising at least one heteroatom selected from N, O or S" includes 4-, 5-, or 6-membered saturated heterocyclic ring comprising at least one heteroatom selected from N, O or S as defined herein. It also includes 4-, 5-, or 6-membered unsaturated heterocyclic ring comprising at least one heteroatom selected from N, O or S.

As used herein, the term "bicyclic aromatic ring system optionally further comprising one or two heteroatoms selected from N, O or S" includes, but is not limited to, imidazopyridine and isothiazolopyridine.

As used herein, the term "bicycloC$_5$-C$_8$alkyl" refers to bicyclic hydrocarbon groups comprising 5 to 8 carbon atoms including, but not limited to, bicyclo[2.1.1]hexyl, bicyclo[1.1.1]pentyl, bicyclo[2.2.1]heptanyl, bicyclo[2.2.2]octyl.

As used herein, the term "optionally substituted" as used in the description of R$^Y$, R$^X$ and R$^Y$ together, R$^{Y2}$, R$^{Y3}$, R$^{Y4}$ includes unsubstituted or substituted once or twice.

As used herein, the term "substituted" as used, for example in the description of R$^{Y2}$, two R$^{Y5}$, includes substituted once or twice, preferably once.

As used herein, the term "more than once" when referring to substituent R$^4$, includes 2, 3, 4, 5, or 6 times. Preferably, it includes 2 or 3 times.

In an embodiment of the invention, the FGFR4 inhibitor used in the combination of the invention is a compound in free form or in pharmaceutically acceptable salt form as described in the examples of patent application WO2015059668.

Therefore, in an embodiment, the FGFR4 inhibitor used in the combination of the invention is a compound in free form or in pharmaceutically acceptable salt form selected from the group consisting of:

7-formyl-N-(5-(trifluoromethyl)pyridin-2-yl)-3,4-dihydro-1,8-naphthyridine-1(2H)-carboxamide;
N-(4,5-dichloropyridin-2-yl)-7-formyl-3,4-dihydro-1,8-naphthyridine-1(2H)-carboxamide;
N-(5-cyanopyridin-2-yl)-7-formyl-3,4-dihydro-1,8-naphthyridine-1(2H)-carboxamide;
N-(5-chloropyridin-2-yl)-7-formyl-3,4-dihydro-1,8-naphthyridine-1(2H)-carboxamide;
7-formyl-N-(pyridin-2-yl)-3,4-dihydro-1,8-naphthyridine-1(2H)-carboxamide;
N-(4,5-dimethylpyridin-2-yl)-7-formyl-3,4-dihydro-1,8-naphthyridine-1(2H)-carboxamide;
7-formyl-N-(5-methylpyridin-2-yl)-3,4-dihydro-1,8-naphthyridine-1(2H)-carboxamide;
N-(5-cyanopyrimidin-2-yl)-7-formyl-3,4-dihydro-1,8-naphthyridine-1(2H)-carboxamide;
6-formyl-N-(5-methylpyridin-2-yl)-2H-pyrido[3,2-b][1,4]oxazine-4(3H)-carboxamide;
6-chloro-N-(5-cyanopyridin-2-yl)-7-formyl-3,4-dihydro-1,8-naphthyridine-1(2H)-carboxamide;
7-formyl-N-(6-methoxypyrimidin-4-yl)-3,4-dihydro-1,8-naphthyridine-1(2H)-carboxamide;
N-(5-cyanopyrazin-2-yl)-7-formyl-3,4-dihydro-1,8-naphthyridine-1(2H)-carboxamide;
N-(5-cyano-4-methoxypyridin-2-yl)-7-formyl-3,4-dihydro-1,8-naphthyridine-1(2H)-carboxamide;
6-formyl-N-(5-(trifluoromethyl)pyridin-2-yl)-2H-pyrido[3,2-b][1,4]oxazine-4(3H)-carboxamide;
6-fluoro-7-formyl-N-(5-(trifluoromethyl)pyridin-2-yl)-3,4-dihydro-1,8-naphthyridine-1(2H)-carboxamide;
N-(5-chloro-4-((2-(isopropylsulfonyl)phenyl)amino)pyrimidin-2-yl)-7-formyl-3,4-dihydro-1,8-naphthyridine-1(2H)-carboxamide;
N-(4,5-dicyanopyridin-2-yl)-7-formyl-3,4-dihydro-1,8-naphthyridine-1(2H)-carboxamide;
7-formyl-6-(hydroxymethyl)-N-(5-(trifluoromethyl)pyridin-2-yl)-3,4-dihydro-1,8-naphthyridine-1(2H)-carboxamide;
N-(5-cyano-4-ethoxypyridin-2-yl)-7-formyl-3,4-dihydro-1,8-naphthyridine-1(2H)-carboxamide;
7-formyl-6-methyl-N-(5-(trifluoromethyl)pyridin-2-yl)-3,4-dihydro-1,8-naphthyridine-1(2H)-carboxamide;
N-(5-cyanopyridin-2-yl)-7-formyl-6-methyl-3,4-dihydro-1,8-naphthyridine-1(2H)-carboxamide;
7-formyl-N-(5-(1-hydroxypentyl)pyridin-2-yl)-3,4-dihydro-1,8-naphthyridine-1(2H)-carboxamide;
N-(5-cyano-4-(2-methoxyethoxy)pyridin-2-yl)-7-formyl-3,4-dihydro-1,8-naphthyridine-1(2H)-carboxamide;
N-(4-chloro-5-cyanopyridin-2-yl)-7-formyl-3,4-dihydro-1,8-naphthyridine-1(2H)-carboxamide;
N-(5-cyano-4-morpholinopyridin-2-yl)-7-formyl-3,4-dihydro-1,8-naphthyridine-1(2H)-carboxamide;
N-(5-cyano-4-(4-hydroxy-4-methylpiperidin-1-yl)pyridin-2-yl)-7-formyl-3,4-dihydro-1,8-naphthyridine-1(2H)-carboxamide;
N-(5-cyanopyridin-2-yl)-7-formyl-6-(hydroxymethyl)-3,4-dihydro-1,8-naphthyridine-1(2H)-carboxamide;
N-(5-cyano-4-(2-methyl-2,8-diazaspiro[4.5]decan-8-yl)pyridin-2-yl)-7-formyl-3,4-dihydro-1,8-naphthyridine-1(2H)-carboxamide;
N-(5-cyanopyridin-2-yl)-6-cyclopropyl-7-formyl-3,4-dihydro-1,8-naphthyridine-1(2H)-carboxamide;
N-(5-cyano-4-(3,6-dihydro-2H-pyran-4-yl)pyridin-2-yl)-7-formyl-3,4-dihydro-1,8-naphthyridine-1(2H)-carboxamide;
N-(5-cyano-4-(tetrahydro-2H-pyran-4-yl)pyridin-2-yl)-7-formyl-3,4-dihydro-1,8-naphthyridine-1(2H)-carboxamide;
N-(5-chloro-4-((tetrahydrofuran-3-yl)oxy)pyrimidin-2-yl)-7-formyl-3,4-dihydro-1,8-naphthyridine-1(2H)-carboxamide;
N-(5-cyano-4-isopropoxypyridin-2-yl)-7-formyl-3,4-dihydro-1,8-naphthyridine-1(2H)-carboxamide;
N-(5-cyano-4-((tetrahydrofuran-2-yl)methoxy)pyridin-2-yl)-7-formyl-3,4-dihydro-1,8-naphthyridine-1(2H)-carboxamide;
N-(5-cyano-4-(oxetan-2-ylmethoxy)pyridin-2-yl)-7-formyl-3,4-dihydro-1,8-naphthyridine-1(2H)-carboxamide;
N-(5-cyano-4-((tetrahydro-2H-pyran-2-yl)methoxy)pyridin-2-yl)-7-formyl-3,4-dihydro-1,8-naphthyridine-1(2H)-carboxamide;
N-(5-cyanopyridin-2-yl)-6-(difluoromethyl)-7-formyl-3,4-dihydro-1,8-naphthyridine-1(2H)-carboxamide;
N-(5-cyano-4-(2-(dimethylamino)ethoxy)pyridin-2-yl)-7-formyl-3,4-dihydro-1,8-naphthyridine-1(2H)-carboxamide;
N-(5-cyano-4-(2-methoxyethoxy)pyridin-2-yl)-7-formyl-6-(hydroxymethyl)-3,4-dihydro-1,8-naphthyridine-1(2H)-carboxamide;
N-(5-cyano-4-((tetrahydrofuran-3-yl)oxy)pyridin-2-yl)-7-formyl-3,4-dihydro-1,8-naphthyridine-1(2H)-carboxamide;
N-(5-cyano-4-(4-hydroxy-4-methylpiperidin-1-yl)pyridin-2-yl)-7-formyl-6-(hydroxymethyl)-3,4-dihydro-1,8-naphthyridine-1(2H)-carboxamide;
7-acetyl-N-(5-cyanopyridin-2-yl)-6-((dimethylamino)methyl)-3,4-dihydro-1,8-naphthyridine-1(2H)-carboxamide;
N-(5-cyano-4-((tetrahydrofuran-2-yl)methoxy)pyridin-2-yl)-7-formyl-6-(hydroxymethyl)-3,4-dihydro-1,8-naphthyridine-1(2H)-carboxamide;
N-(5-cyano-4-((tetrahydro-2H-pyran-2-yl) methoxy)pyridin-2-yl)-7-formyl-6-(hydroxymethyl)-3,4-dihydro-1,8-naphthyridine-1(2H)-carboxamide;

N-(5-cyano-4-(2-methyl-2,8-diazaspiro[4.5]decan-8-yl)
pyridin-2-yl)-7-formyl-6-(hydroxymethyl)-3,4-dihydro-
1,8-naphthyridine-1(2H)-carboxamide;

N-(5-cyano-4-((1-methyl pyrrolidin-3-yl)oxy)pyridin-2-yl)-
7-formyl-6-(hydroxymethyl)-3,4-dihydro-1,8-naphthyri-
dine-1(2H)-carboxamide;

N-(5-cyano-4-((1-methylpiperidin-4-yl)oxy)pyridin-2-yl)-
7-formyl-6-(hydroxymethyl)-3,4-dihydro-1,8-naphthyri-
dine-1(2H)-carboxamide;

N-(5-cyano-4-((1-methoxypropan-2-yl)oxy)pyridin-2-yl)-7-
formyl-6-(hydroxymethyl)-3,4-dihydro-1,8-naphthyri-
dine-1(2H)-carboxamide;

N-(5-cyano-4-((tetrahydrofuran-3-yl)oxy)pyridin-2-yl)-7-
formyl-6-(hydroxymethyl)-3,4-dihydro-1,8-naphthyri-
dine-1(2H)-carboxamide;

N-(5-cyano-4-((tetrahydrofuran-3-yl)oxy)pyridin-2-yl)-6-
((dimethylamino)methyl)-7-formyl-3,4-dihydro-1,8-
naphthyridine-1(2H)-carboxamide;

2-(8-((5-cyanopyridin-2-yl)carbamoyl)-2-formyl-5,6,7,8-
tetrahydro-1,8-naphthyridin-3-yl)acetic acid;

N-(5-cyano-4-((tetrahydro-2H-pyran-4-yl)oxy)pyridin-2-
yl)-7-formyl-6-(hydroxymethyl)-3,4-dihydro-1,8-naph-
thyridine-1(2H)-carboxamide;

N-(5-cyano-4-((1-methyl pyrrolidin-3-yl)oxy)pyridin-2-yl)-
7-formyl-6-(hydroxymethyl)-3,4-dihydro-1,8-naphthyri-
dine-1(2H)-carboxamide;

N-(5-cyano-4-(((tetrahydro-2H-pyran-3-yl)methyl)amino)
pyridin-2-yl)-7-formyl-6-(hydroxymethyl)-3,4-dihydro-
1,8-naphthyridine-1(2H)-carboxamide;

N-(5-cyano-4-((tetrahydrofuran-3-yl)amino)pyridin-2-yl)-
7-formyl-6-(hydroxymethyl)-3,4-dihydro-1,8-naphthyri-
dine-1(2H)-carboxamide;

N-(5-cyano-4-((2-methoxypropyl)amino)pyridin-2-yl)-7-
formyl-6-(hydroxymethyl)-3,4-dihydro-1,8-naphthyri-
dine-1(2H)-carboxamide;

N-(5-chloro-44(1-methoxypropan-2-yl)oxy)pyrimidin-2-
yl)-7-formyl-6-(hydroxymethyl)-3,4-dihydro-1,8-naph-
thyridine-1(2H)-carboxamide;

N-(4-(4-chloro-2-hydroxybutoxy)-5-cyanopyridin-2-yl)-7-
formyl-6-(hydroxymethyl)-3,4-dihydro-1,8-naphthyri-
dine-1(2H)-carboxamide;

N-(5-cyano-4-(2-methoxyethoxy)pyridin-2-yl)-7-formyl-6-
(trifluoromethyl)-3,4-dihydro-1,8-naphthyridine-1(2H)-
carboxamide;

N-(5-cyano-4-(2-methoxyethoxy)pyridin-2-yl)-6-cyclopro-
pyl-7-formyl-3,4-dihydro-1,8-naphthyridine-1(2H)-car-
boxamide;

N-(5-cyano-4-(2-methoxyethoxy)pyridin-2-yl)-6-(difluo-
romethyl)-7-formyl-3,4-dihydro-1,8-naphthyridine-1
(2H)-carboxamide;

N-(5-cyano-4-(2-methoxyethoxy)pyridin-2-yl)-6-((dimeth-
ylamino)methyl)-7-formyl-3,4-dihydro-1,8-naphthyri-
dine-1(2H)-carboxamide;

N-(5-cyano-4-((3-(hydroxymethyl)bicyclo[2.2.1]heptan-2-
yl)amino)pyridin-2-yl)-7-formyl-6-(hydroxymethyl)-3,4-
dihydro-1,8-naphthyridine-1(2H)-carboxamide;

N-(5-cyano-4-((tetrahydro-2H-pyran-4-yl)amino)pyridin-2-
yl)-7-formyl-6-(hydroxymethyl)-3,4-dihydro-1,8-naph-
thyridine-1(2H)-carboxamide;

N-(5-cyano-4-(2-m ethoxyethoxy)pyridin-2-yl)-7-formyl-6-
(methoxymethyl)-3,4-dihydro-1,8-naphthyridine-1(2H)-
carboxamide;

N-(5-cyanopyridin-2-yl)-7-formyl-6-((N-methylacetamido)
methyl)-3,4-dihydro-1,8-naphthyridine-1(2H)-carboxam-
ide;

N-(5-chloro-4-((tetrahydrofuran-3-yl)oxy)pyrimidin-2-yl)-
7-formyl-6-(hydroxymethyl)-3,4-dihydro-1,8-naphthyri-
dine-1(2H)-carboxamide;

N-(5-cyano-4-((tetrahydrofuran-3-yl)oxy)pyrimidin-2-yl)-
7-formyl-6-(hydroxymethyl)-3,4-dihydro-1,8-naphthyri-
dine-1(2H)-carboxamide;

7-formyl-6-(hydroxymethyl)-N-(4-((tetrahydrofuran-3-yl)
oxy)pyridin-2-yl)-3,4-dihydro-1,8-naphthyridine-1(2H)-
carboxamide;

N-(5-chloro-4-((tetrahydrofuran-3-yl)oxy)pyridin-2-yl)-7-
formyl-6-(hydroxymethyl)-3,4-dihydro-1,8-naphthyri-
dine-1(2H)-carboxamide;

N-(5-cyano-4-((1-methylpiperidin-3-yl) methoxy)pyridin-
2-yl)-7-formyl-6-(hydroxymethyl)-3,4-dihydro-1,8-naph-
thyridine-1(2H)-carboxamide;

N-(5-cyano-4-((1-methyl pyrrolidin-2-yl) methoxy)pyridin-
2-yl)-7-formyl-6-(hydroxymethyl)-3,4-dihydro-1,8-naph-
thyridine-1(2H)-carboxamide;

N-(5-cyano-4-((1-methylpiperidin-2-yl) methoxy)pyridin-
2-yl)-7-formyl-6-(hydroxymethyl)-3,4-dihydro-1,8-naph-
thyridine-1(2H)-carboxamide;

N-(5-fluoropyridin-2-yl)-7-formyl-6-(hydroxymethyl)-3,4-
dihydro-1,8-naphthyridine-1(2H)-carboxamide;

N-(5-cyano-4-(2-(dimethylamino)ethoxy)pyridin-2-yl)-6-
form-$^{13}$C-yl-2H-pyrido[3,2-b][1,4]oxazine-4(3H)-car-
boxamide;

N-(5-cyano-4-((1-methylpiperidin-4-yl)methoxy)pyridin-2-
yl)-7-formyl-6-(hydroxymethyl)-3,4-dihydro-1,8-naph-
thyridine-1(2H)-carboxamide;

N-(5-cyanopyridin-2-yl)-7-formyl-4-hydroxy-3,4-dihydro-
1,8-naphthyridine-1(2H)-carboxamide;

N-(5-cyano-4-((2-methoxyethyl)amino)pyridin-2-yl)-7-
formyl-6-(hydroxymethyl)-3,4-dihydro-1,8-naphthyri-
dine-1(2H)-carboxamide;

N-(5-cyano-4-(2-((dimethylamino)methyl)morpholino)
pyridin-2-yl)-7-formyl-6-(hydroxymethyl)-3,4-dihydro-
1,8-naphthyridine-1(2H)-carboxamide;

N-(5-cyano-4-(quinuclidin-3-yloxy)pyridin-2-yl)-7-formyl-
6-(hydroxymethyl)-3,4-dihydro-1,8-naphthyridine-1
(2H)-carboxamide;

N-(5-cyano-4-((2-methoxyethyl)amino)pyridin-2-yl)-7-
formyl-6-((4-methyl-2-oxopiperazin-1-yl)methyl)-3,4-di-
hydro-1,8-naphthyridine-1(2H)-carboxamide;

7-formyl-6-(hydroxymethyl)-N-(44(2-methoxyethyl)
amino)-5-(trifluoromethyl)pyridin-2-yl)-3,4-dihydro-1,8-
naphthyridine-1(2H)-carboxamide;

N-(5-cyano-4-(4-((dimethylamino)methyl)-4-hydroxypip-
eridin-1-yl)pyridin-2-yl)-7-formyl-6-(hydroxymethyl)-3,
4-dihydro-1,8-naphthyridine-1(2H)-carboxamide;

N-(5-cyano-4-((2-hydroxy-2-methylpropyl)amino)pyridin-
2-yl)-7-formyl-6-(hydroxymethyl)-3,4-dihydro-1,8-naph-
thyridine-1(2H)-carboxamide;

N-(5-cyano-4-((3-(dimethylamino)-2-hydroxy-2-methyl-
propyl)amino)pyridin-2-yl)-7-formyl-6-(hydroxym-
ethyl)-3,4-dihydro-1,8-naphthyridine-1(2H)-carboxam-
ide;

N-(5-cyano-4-((2-fluoroethyl)amino)pyridin-2-yl)-7-
formyl-6-(hydroxymethyl)-3,4-dihydro-1,8-naphthyri-
dine-1(2H)-carboxamide;

N-(5-cyano-4-(2,2,2-trifluoroethoxy)pyridin-2-yl)-7-
formyl-6-(hydroxymethyl)-3,4-dihydro-1,8-naphthyri-
dine-1(2H)-carboxamide;

N-(5-cyano-4-isopropoxypyridin-2-yl)-7-formyl-6-((4-
methyl-2-oxopiperazin-1-yl)methyl)-3,4-dihydro-1,8-
naphthyridine-1(2H)-carboxamide;

N-(5-cyano-4-(isopropylamino)pyridin-2-yl)-7-formyl-6-((4-methyl-2-oxopiperazin-1-yl)methyl)-3,4-dihydro-1,8-naphthyridine-1(2H)-carboxamide;

N-(5-cyano-4-((2-methoxyethyl)amino)pyridin-2-yl)-7-formyl-6-((3-oxomorpholino)methyl)-3,4-dihydro-1,8-naphthyridine-1(2H)-carboxamide;

N-(5-cyano-4-((2-methoxyethyl)amino)pyridin-2-yl)-7-formyl-6-((3-hydroxy-2-oxopyrrolidin-1-yl)methyl)-3,4-dihydro-1,8-naphthyridine-1(2H)-carboxamide;

N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide;

N-(5-cyano-4-ethylpyridin-2-yl)-6,7-diformyl-3,4-dihydro-1,8-naphthyridine-1(2H)-carboxamide;

N-(5-cyano-4-((2-methoxyethyl)amino)pyridin-2-yl)-7-formyl-6-((2-oxopiperazin-1-yl)methyl)-3,4-dihydro-1,8-naphthyridine-1(2H)-carboxamide hydrochloride;

N-(5-cyano-4-((1-methoxypropan-2-yl)oxy)pyridin-2-yl)-7-formyl-6-((4-methyl-2-oxooxazolidin-3-yl)methyl)-3,4-dihydro-1,8-naphthyridine-1(2H)-carboxamide;

N-(5-cyano-4-((2-methoxyethyl)amino)pyridin-2-yl)-7-formyl-6-((3-methyl-5-oxomorpholino)methyl)-3,4-dihydro-1,8-naphthyridine-1(2H)-carboxamide;

6-((4-acetyl piperazin-1-yl)methyl)-N-(5-cyano-4-isopropoxypyridin-2-yl)-7-formyl-3,4-dihydro-1,8-naphthyridine-1(2H)-carboxamide;

N-(5-cyano-4-((2-methoxyethyl)amino)pyridin-2-yl)-7-formyl-6-(1-(N-methylacetamido)ethyl)-3,4-dihydro-1,8-naphthyridine-1(2H)-carboxamide;

N-(5-cyano-4-isopropoxypyridin-2-yl)-7-formyl-6-((2-hydroxy-N-methylacetamido)methyl)-3,4-dihydro-1,8-naphthyridine-1(2H)-carboxamide;

N-(5-cyano-4-((2-methoxyethyl)amino)pyridin-2-yl)-6-((N-(2-(dimethylamino)ethyl)acetamido)methyl)-7-formyl-3,4-dihydro-1,8-naphthyridine-1(2H)-carboxamide;

N-(5-cyano-4-((2-methoxyethyl)amino)pyridin-2-yl)-6-((N-(2-(dimethylamino)ethyl)methylsulfonamido)methyl)-7-formyl-3,4-dihydro-1,8-naphthyridine-1(2H)-carboxamide;

N-(5-cyano-4-isopropoxypyridin-2-yl)-6-((2-(dimethylamino)-N-methylacetamido)methyl)-7-formyl-3,4-dihydro-1,8-naphthyridine-1(2H)-carboxamide;

N-(5-cyano-4-((2-methoxyethyl)amino)pyridin-2-yl)-7-formyl-6-((2-methoxy-N-methylacetamido)methyl)-3,4-dihydro-1,8-naphthyridine-1(2H)-carboxamide;

N-(5-cyano-4-((2-methoxyethyl)amino)pyridin-2-yl)-7-formyl-6-((3-oxothiomorpholino)methyl)-3,4-dihydro-1,8-naphthyridine-1(2H)-carboxamide;

N-(5-cyano-4-((2-methoxyethyl)amino)pyridin-2-yl)-6-((1,1-dioxido-3-oxothiomorpholino)methyl)-7-formyl-3,4-dihydro-1,8-naphthyridine-1(2H)-carboxamide;

N-(5-cyano-4-(((4-methylmorpholin-2-yl)methyl)amino)pyridin-2-yl)-6-(difluoromethyl)-7-formyl-3,4-dihydro-1,8-naphthyridine-1(2H)-carboxamide;

N-(5-cyano-4-((1,1,1-trifluoro-3-methoxypropan-2-yl)oxy)pyridin-2-yl)-6-(difluoromethyl)-7-formyl-3,4-dihydro-1,8-naphthyridine-1(2H)-carboxamide;

N-(5-cyano-4-((2-(trifluoromethoxy)ethyl)amino)pyridin-2-yl)-7-formyl-6-((N-methylacetamido)methyl)-3,4-dihydro-1,8-naphthyridine-1(2H)-carboxamide;

6-(2-oxa-5-azaspiro[3.4]octan-5-ylmethyl)-N-(5-cyano-4-((2-methoxyethyl)amino)pyridin-2-yl)-7-formyl-3,4-dihydro-1,8-naphthyridine-1(2H)-carboxamide;

N-(4-((2-(tert-butoxy)ethyl)amino)-5-cyanopyridin-2-yl)-7-formyl-6-((4-methyl-2-oxopiperazin-1-yl)methyl)-3,4-dihydro-1,8-naphthyridine-1(2H)-carboxamide;

N-(5-cyano-4-((2-hydroxyethyl)amino)pyridin-2-yl)-7-formyl-6-((4-methyl-2-oxopiperazin-1-yl)methyl)-3,4-dihydro-1,8-naphthyridine-1(2H)-carboxamide;

N-(5-cyano-4-(2-hydroxyethoxy)pyridin-2-yl)-7-formyl-6-((4-methyl-2-oxopiperazin-1-yl)methyl)-3,4-dihydro-1,8-naphthyridine-1(2H)-carboxamide;

N-(5-cyanopyridin-2-yl)-2-formyl-7,8-dihydro-5H-pyrido[2,3-b]azepine-9(6H)-carboxamide;

N-(5-cyano-4-(2-methoxyethoxy)pyridin-2-yl)-2-formyl-7,8-dihydro-5H-pyrido[2,3-b]azepine-9(6H)-carboxamide;

N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide;

7-formyl-N-(1-isopropyl-1H-imidazo[4,5-c]pyridin-6-yl)-6-((4-methyl-2-oxopiperazin-1-yl)methyl)-3,4-dihydro-1,8-naphthyridine-1(2H)-carboxamide;

7-formyl-N-(1-isopropyl-1H-imidazo[4,5-c]pyridin-6-yl)-6-((2-oxopyrrolidin-1-yl)methyl)-3,4-dihydro-1,8-naphthyridine-1(2H)-carboxamide;

4-((8-((5-cyano-4-((2-methoxyethyl)amino)pyridin-2-yl)carbamoyl)-2-formyl-5,6,7,8-tetrahydro-1,8-naphthyridin-3-yl)methyl)-1-methyl-3-oxopiperazine 1-oxide;

N-(5-cyano-4-((2-oxopiperidin-4-yl)methoxy)pyridin-2-yl)-7-formyl-6-((2-oxopyrrolidin-1-yl)methyl)-3,4-dihydro-1,8-naphthyridine-1(2H)-carboxamide;

N-(5-cyano-4-(2-methoxyethoxy)pyridin-2-yl)-7-formyl-2-methyl-6-((4-methyl-2-oxopiperazin-1-yl)methyl)-3,4-dihydro-1,8-naphthyridine-1(2H)-carboxamide;

N-(5-cyano-4-isopropoxypyridin-2-yl)-7-formyl-2-methyl-6-((4-methyl-2-oxopiperazin-1-yl)methyl)-3,4-dihydro-1,8-naphthyridine-1(2H)-carboxamide;

N-(5-cyano-4-((2-methoxyethyl)amino)pyridin-2-yl)-7-formyl-2-methyl-6-((4-methyl-2-oxopiperazin-1-yl)methyl)-3,4-dihydro-1,8-naphthyridine-1(2H)-carboxamide;

N-(5-cyano-4-((2-methoxyethyl)amino)pyridin-2-yl)-7-formyl-6-((3-hydroxy-4-methyl-2-oxopiperazin-1-yl)methyl)-3,4-dihydro-1,8-naphthyridine-1(2H)-carboxamide;

N-(5-cyano-4-isopropoxypyridin-2-yl)-6-formyl-2,3-dihydro-1H-pyrrolo[2,3-b]pyridine-1-carboxamide;

2-((5-cyano-2-(7-formyl-6-((4-methyl-2-oxopiperazin-1-yl)methyl)-1,2,3,4-tetrahydro-1,8-naphthyridine-1-carboxamido)pyridin-4-yl)amino)ethyl hydrogen sulfate;

N-(4-(bicyclo[1.1.1]pentan-1-ylamino)-5-cyanopyridin-2-yl)-7-formyl-6-((4-methyl-2-oxopiperazin-1-yl)methyl)-3,4-dihydro-1,8-naphthyridine-1(2H)-carboxamide;

N-(5-cyano-4-(thiophen-2-ylmethoxy)pyridin-2-yl)-7-formyl-6-((N-methylacetamido)methyl)-3,4-dihydro-1,8-naphthyridine-1(2H)-carboxamide;

N-(5-cyano-4-(isopropylthio)pyridin-2-yl)-7-formyl-6-((N-methylacetamido)methyl)-3,4-dihydro-1,8-naphthyridine-1(2H)-carboxamide;

N-(5-cyano-4-((2-methoxyethyl)amino)pyridin-2-yl)-6-((3,5-dimethylpiperazin-1-yl)methyl)-7-formyl-3,4-dihydro-1,8-naphthyridine-1(2H)-carboxamide;

N-(5-cyano-4-((2-methoxyethyl)amino)pyridin-2-yl)-7-formyl-6-((3,3,4-trimethyl-2-oxopiperazin-1-yl)methyl)-3,4-dihydro-1,8-naphthyridine-1(2H)-carboxamide;

6-amino-N-(5-cyanopyridin-2-yl)-7-formyl-3,4-dihydro-1,8-naphthyridine-1(2H)-carboxamide;

N-(5-cyano-4-((2-methoxyethyl)amino)pyridin-2-yl)-7-formyl-6-(tetrahydro-2H-pyran-4-yl)-3,4-dihydro-1,8-naphthyridine-1(2H)-carboxamide;

N-(5-cyano-4-((2-methoxyethyl)amino)pyridin-2-yl)-6-(1,3-dimethyl-1H-pyrazol-4-yl)-7-formyl-3,4-dihydro-1,8-naphthyridine-1(2H)-carboxamide;

N-(5-cyano-4-((2-methoxyethyl)amino)pyridin-2-yl)-7-formyl-6-(1-methyl-1H-pyrazol-4-yl)-3,4-dihydro-1,8-naphthyridine-1(2H)-carboxamide;
N-(5-cyano-4-((2-methoxyethyl)amino)pyridin-2-yl)-7-formyl-6-(2-methylthiazol-5-yl)-3,4-dihydro-1,8-naphthyridine-1(2H)-carboxamide;
N-(5-cyano-4-((2-methoxyethyl)amino)pyridin-2-yl)-7-formyl-6-(thiophen-2-yl)-3,4-dihydro-1,8-naphthyridine-1(2H)-carboxamide;
N-(5-cyano-4-((2-methoxyethyl)amino)pyridin-2-yl)-7-formyl-6-(1H-imidazol-1-yl)-3,4-dihydro-1,8-naphthyridine-1(2H)-carboxamide;
N-(5-cyano-4-((2-methoxyethyl)amino)pyridin-2-yl)-7-formyl-6-(pyridin-3-yl)-3,4-dihydro-1,8-naphthyridine-1(2H)-carboxamide;
N-(5-cyano-4-((2-methoxyethyl)amino)pyridin-2-yl)-7-formyl-6-(1-methyl-1H-pyrazol-5-yl)-3,4-dihydro-1,8-naphthyridine-1(2H)-carboxamide;
N-(5-cyano-4-((2-methoxyethyl)amino)pyridin-2-yl)-7-formyl-6-(3-methyl-1H-1,2,4-triazol-1-yl)-3,4-dihydro-1,8-naphthyridine-1(2H)-carboxamide;
N-(5-cyano-4-((2-methoxyethyl)amino)pyridin-2-yl)-7-formyl-6-(3-methyl-2-oxopyrrolidin-1-yl)-3,4-dihydro-1,8-naphthyridine-1(2H)-carboxamide;
N-(5-cyano-4-((2-methoxyethyl)amino)pyridin-2-yl)-7-formyl-6-(3-oxomorpholino)-3,4-dihydro-1,8-naphthyridine-1(2H)-carboxamide;
N-(5-cyano-4-((2-methoxyethyl)amino)pyridin-2-yl)-7-formyl-6-(2-oxooxazolidin-3-yl)-3,4-dihydro-1,8-naphthyridine-1(2H)-carboxamide;
N-(5-cyano-4-isopropoxypyridin-2-yl)-7-formyl-6-(tetrahydrofuran-3-yl)-3,4-dihydro-1,8-naphthyridine-1(2H)-carboxamide;
N-(5-cyano-4-isopropoxypyridin-2-yl)-7-formyl-6-(piperidin-4-yl)-3,4-dihydro-1,8-naphthyridine-1(2H)-carboxamide;
N-(5-cyano-4-((2-methoxyethyl)amino)pyridin-2-yl)-7-formyl-6-(1-(oxetan-3-yl)piperidin-4-yl)-3,4-dihydro-1,8-naphthyridine-1(2H)-carboxamide; and
N-(5-cyano-4-((2-methoxyethyl)amino)pyridin-2-yl)-6-(1-(2,2-difluoroethyl)piperidin-4-yl)-7-formyl-3,4-dihydro-1,8-naphthyridine-1(2H)-carboxamide,
in free form or in pharmaceutically acceptable salt form.

Patent application WO2015/059668 describes how to make the compounds of formula (I) and the specific compounds described above. Dosages of the active ingredients and therapeutic regimens of the combination of the invention may be determined by a skilled artisan.

In a preferred embodiment of the invention, the FGFR4 inhibitor used in the combination of the invention is N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form.

N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide is also referred to herein as Compound A (Cpd A). Compound A is a highly selective FGFR4 inhibitor, which inhibits FGFR4 with an IC50 of 1.1 nM. In biochemical assays, it showed at least 1,000 fold selectivity against of panel of 65 kinases and in a kinome wide scan, consisting of 456 kinases, FGFR4 was the only target of Compound A (see Porta et al, Abstract 2098, Proceedings: AACR Annual Meeting 2017; Apr. 1-5, 2017). Compound A is also known as FGF401, and has shown promising clinical activity in patients with advanced HCC (see Chan et al, Proceedings: AACR Annual Meeting 2017; Apr. 1-5, 2017).

N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide is described specifically in example 83 of patent application WO2015/059668 and has the following structure:

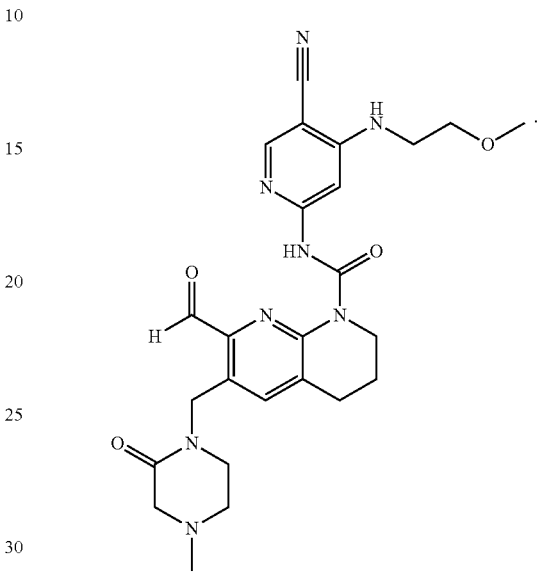

In an embodiment of the invention, the FGFR4 inhibitor is N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form.

In an embodiment, the FGFR4 inhibitor is N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in salt form, preferably a salt form described in example 83 of patent application WO2015059668.

In an embodiment of the invention, the FGFR4 inhibitor is N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form.

The FGFR4 inhibitor of the combination of the present invention, i.e. N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide may be administered at a therapeutically effective total daily dose of about 25-200 mg, or about 50-150 mg (e.g., once per day). The total daily dose of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (e.g. in citric acid salt form) which is administered may be 50 mg, 80 mg, 100 mg, 120 mg or 150 mg. In particular N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide may be administered at a dose of 80 mg daily or 120 mg daily.

The dose or dosage of the FGFR4 inhibitor as described herein refers to the amount of the free base. For example, if the dosage quoted is 80 mg, and a pharmaceutically acceptable salt of the FGFR4 inhibitor is used, such as the citrate salt thereof, the dose of 80 mg corresponds to the amount of free base of the FGFR4 inhibitor, namely N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide.

In a 4-week dog study where Compound A was administered, increases in ALT and AST occurred in individual dogs at all dose groups with no dose dependency. The maximal increase was 6-fold and ≤2-fold for ALT and AST respectively (relative to pre-dose values), and occurred during week 2 of the study. Generally, there was no further increase in transaminase levels despite continued dosing over the 4-weeks indicating a level of adaptation to these pharmacologically mediated effects. Recovery was evident by day 8 following cessation of Compound A administration. A bile acid sequestrant such as Cholestyramine (CHO) mitigated and reversed Compound A-mediated ALT increases in dogs, suggesting that the increase in ALT observed following administration of FGF401 is likely secondary to increases in bile acids.

Based on these observations and the Examples, it is predicted that selective FGFR4 inhibitors such as Compound A may provide an effective therapeutic option for patients suffering from cancers, in particular liver cancer and HCC, since side-effects may be reversed and managed by the concomitant or sequential administration of a bile acid sequestrant, despite the risk of a lack of efficacy.

FGFR4 inhibitors used in the present invention may be used for the treatment of proliferative diseases such as cancer, in particular liver cancer, breast cancer, glioblastoma, prostate cancer, rhabdomyosarcoma, gastric cancer, ovarian cancer, lung cancer, colon cancer, more particularly liver cancer.

As used herein "liver cancer" also refers to hepatocellular carcinoma (HCC).

The FGFR4 inhibitor may be used in the pharmaceutical combination of the invention as a standalone pharmaceutical composition comprising said FGFR4 inhibitor and one or more pharmaceutically acceptable carriers.

Similarly, the bile acid sequestrant may be used in the pharmaceutical combination of the invention as a standalone pharmaceutical composition comprising the bile acid sequestrant and one or more pharmaceutically acceptable carriers.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington The Science and Practice of Pharmacy, $22^{nd}$ Ed. Pharmaceutical Press, 2013, pp. 1049-1070). Except insofar as any conventional carrier is incompatible with the active ingredient, its use in the therapeutic or pharmaceutical compositions is contemplated.

The term "a therapeutically effective amount" or "therapeutically effective level" of a compound of the combination of the present invention refers to an amount of the compound of the present combination that will elicit the biological or medical response of a subject, for example, reduction or inhibition of an enzyme or a protein activity, or ameliorate symptoms, alleviate conditions, slow or delay disease progression, or prevent a disease, etc.

For instance, in one non-limiting embodiment, the term "a therapeutically effective amount" when referring to the FGFR4 inhibitor refers to the amount of FGFR4 inhibitor compound that, when administered to a subject, is effective to (1) at least partially alleviate, inhibit, prevent and/or ameliorate a condition, or a disorder or a disease (i) mediated by FGFR4, or (ii) associated with FGFR4 activity, or (iii) characterized by activity (normal or abnormal) of FGFR4, or (2) reduce or inhibit the activity of FGFR4; or (3) reduce or inhibit the expression of FGFR4. In another non-limiting embodiment, the term "a therapeutically effective amount" refers to the amount of FGFR4 inhibitor compound that, when administered to a cell, or a tissue, or a non-cellular biological material, or a medium, is effective to at least partially reduce or inhibit the activity of FGFR4.

In another non-limiting embodiment, the term "a therapeutically effective amount" when referring to a bile acid sequestrant refers to the amount of bile acid sequestrant that, when administered to a subject, is effective to at least partially alleviate, inhibit, prevent and/or ameliorate a side effect associated with FGFR4 inhibition therapy. The FGFR inhibition therapy includes administration of an FGFR4 inhibitor, preferably Compound A, or a pharmaceutically acceptable salt, e.g. a citrate salt, thereof.

As used herein, the term "subject" or "patient" refers to a human. The subject or the patient suffers from a proliferative disorder described herein, e.g. a cancer, in particular liver cancer, breast cancer, glioblastoma, prostate cancer, rhabdomyosarcoma, gastric cancer, ovarian cancer, lung cancer, colon cancer, more particularly liver cancer which includes HCC.

Bile acid sequestrants are ion-exchange resins which are used clinically for conditions related to bile acid malabsorption such as diarrhea for example. A review of the clinical uses of bile acid sequestrants is given by Scaldaferri F. et al. in Intern Emerg Med (2013) 8:205-210.

A bile acid sequestrant functionally has the ability to disrupt the enterohepatic circulation of bile acids by combining with bile constituents and preventing their reabsorption from the gut. Examples of bile acid sequestrant include cholestyramine, colesevelam, colesevalam hydrochloride, colestipol or selevamer. In a preferred embodiment of the invention, the bile acid sequestrant is cholestyramine.

Bile acid sequestrants may be used to treat bile acid-induced diarrhea. However, the present invention provides for the first time the use of a bile acid sequestrant, preferably when coadministered with an FGFR4 inhibitor, including a selective FGFR4 inhibitor, to reduce or prevent side-effects associated with FGFR4 inhibition therapy, e.g. an increase in liver enzymes.

A bile acid sequestrant such as cholestyramine may be taken at a daily dose of 4-24 g daily. The recommended dosing schedule of the bile acid sequestrant is maximal 1 to 4 doses daily, but may be administered in 1 to 6 doses per day. Cholestyramine is usually administered as a suspension mixed with water or other liquids.

In another aspect, the invention relates to a pharmaceutical combination of the invention for use as a medicament.

In another aspect, the invention relates to a pharmaceutical combination of the invention for use in the treatment of a disease which may be treated by inhibition of FGFR4. In another embodiment, the invention relates to a pharmaceutical combination of the invention for use in the treatment of cancer. In an embodiment, the cancer is selected from liver cancer, breast cancer, glioblastoma, prostate cancer, rhabdomyosarcoma, gastric cancer, ovarian cancer, lung cancer, colon cancer. In a preferred embodiment, the cancer is liver cancer. As a further embodiment, the invention relates to the use of a pharmaceutical combination of the invention in therapy. In a further embodiment, the therapy is for a disease which may be treated by inhibition of FGFR4. In another embodiment, the disease is cancer. In a further embodiment, the disease is selected from liver cancer, breast cancer, glioblastoma, prostate cancer, rhabdomyosarcoma, gastric cancer, ovarian cancer, lung cancer, colon cancer. In a preferred embodiment, the disease is liver cancer.

In another embodiment, the invention relates to a method of treating a disease which is treated by inhibition of FGFR4 comprising administration of the pharmaceutical combination of the invention. In a further embodiment, the invention relates to a method of treating a disease which is treated by inhibition of FGFR4 comprising administration of the pharmaceutical combination of the invention comprising the simultaneous or sequential administration of an FGFR4 inhibitor and a bile acid sequestrant.

Another aspect of the invention relates to the finding that bile acid sequestrants can be used concomitantly with FGFR4 inhibitors and thereby reduce or prevent side-effects associated with FGFR4 inhibition therapy, e.g. therapy by administration of Compound A, or a pharmaceutically acceptable salt, e.g. a citrate salt, thereof.

Thus, in an embodiment, the invention relates to the use of a bile acid sequestrant for reducing or preventing side-effects associated with FGFR4 inhibition therapy. The FGFR inhibition therapy includes administration of an FGFR4 inhibitor, preferably Compound A, or a pharmaceutically acceptable salt, e.g. a citrate salt, thereof.

In an important aspect of the present invention, the side effects associated with FGFR4 inhibition therapy do not include diarrhea.

In another embodiment, the invention relates to a bile acid sequestrant for use in reducing or preventing side-effects associated with FGFR4 inhibition therapy, wherein the side effect does not include diarrhea. The FGFR inhibition therapy includes administration of an FGFR4 inhibitor, preferably Compound A, or a pharmaceutically acceptable salt, e.g. a citrate salt, thereof.

In an embodiment, the bile acid sequestrant is cholestyramine. In an embodiment, the FGFR4 inhibition therapy comprises the use of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, in particular in citric acid salt form.

In another embodiment, the invention relates to a method for reducing or preventing side effects associated with FGFR4 inhibition therapy comprising administering a bile acid sequestrant to a subject on FGFR4 inhibition therapy.

In another embodiment, the invention relates to a method for diminishing the incidence or severity of side effects associated with FGFR4 inhibition therapy comprising administering to a subject in need of FGFR4 inhibition therapy a combination comprising the simultaneous or sequential administration of a FGFR4 inhibitor and a bile acid sequestrant.

Side-effects associated with FGFR4 inhibition therapy are those which can be observed during treatment with an FGFR4 inhibitor, e.g with Compound A, or a pharmaceutically acceptable salt, e.g. a citrate salt, thereof.

In an embodiment, the side-effect associated with FGFR4 inhibition therapy is liver enzyme elevation.

Liver enzymes, such as alanine aminotransaminase (ALT) and aspartate aminotransferase (AST), when detected in the serum, plasma or blood of a subject, can be indicative of liver inflammation and/or liver damage. Liver enzyme elevation is a serious side-effect. Some symptoms of liver enzyme elevation include fatigue, abdominal pain with jaundice, swelling. In the context of FGFR4 inhibition therapy, an elevated liver enzyme level in the serum, plasma or blood of a subject on FGFR4 inhibition therapy would have the consequence that treatment would have to be discontinued.

In another embodiment, the side-effect associated with FGFR4 inhibition therapy is ALT elevation. In another embodiment, the side-effect associated with FGFR4 inhibition therapy is AST elevation. In another embodiment, the side-effect associated with FGFR4 inhibition therapy is miRNA122 elevation.

As used herein, the term ALT refers to alanine aminotransaminase also known as serum glutamic pyruvic transaminase (SGPT).

As used herein, the term AST refers to aspartate aminotransferase also known as serum glutamic oxaloacetic transaminase (SGOT).

As used herein, the term "liver enzyme elevation" refers to the increase of liver enzyme in the serum, plasma or blood of a subject compared to a normal value as measured by standard tests known in the art. For instance, a normal value for ALT in blood is between 7 and 55 units per liter. Therefore, in an embodiment of the invention, an ALT elevation would mean that more than 55 units per liter are detected in the blood. In an embodiment of the invention, elevated ALT is more than 2 to 3 times the upper limit of the normal level, i.e. more than about 110 to 165 units/liter.

Typically the range for normal AST is between 10 to 40 units per liter. Therefore, in an embodiment of the invention, an AST elevation would mean that more than 40 units per liter are detected in the blood. In an embodiment of the invention, elevated AST is more than 2 to 3 times the upper limit of the normal level, i.e. more than about 80 to 120 units/liter.

In an embodiment, the invention relates to a method of reducing ALT levels to below 55 units per liter of serum, plasma or blood in a patient receiving FGFR4 inhibition therapy, wherein said patient has ALT levels greater than 55 units per liter of serum, plasma or blood, comprising administering to said patient a pharmaceutical combination comprising an FGFR4 inhibitor and a bile acid sequestrant.

In another embodiment, the invention relates to a method of reducing AST levels to below 40 units per liter of serum, plasma or blood in a patient receiving FGFR4 inhibition therapy, wherein said patient has AST levels greater than 40 units per liter of serum, plasma or blood, comprising administering to said patient a pharmaceutical combination comprising an FGFR4 inhibitor and a bile acid sequestrant.

Figure 2:
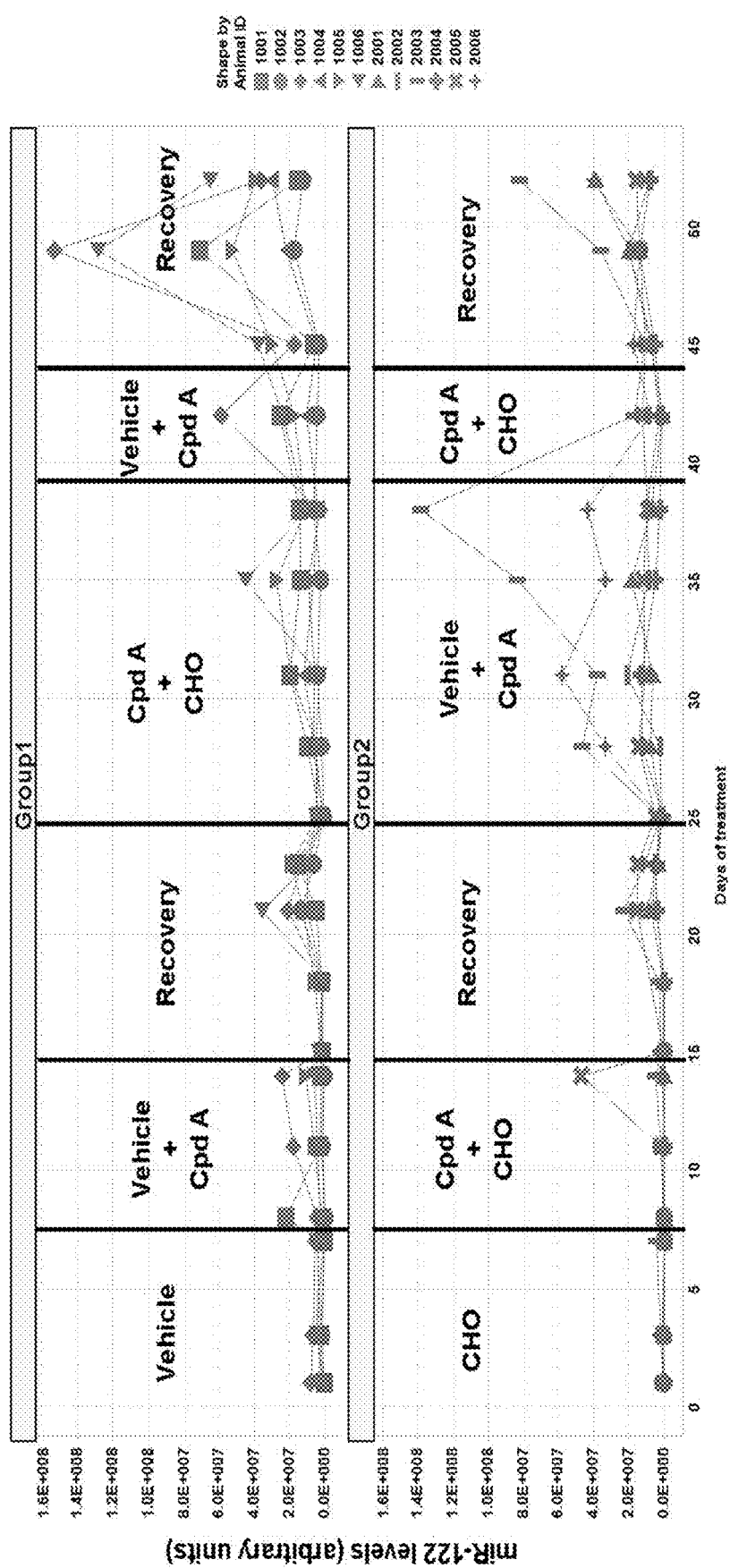
FIG. 2 shows the variation of miRNA122 level in the serum of dogs receiving FGFR4 inhibitor (compound A, abbreviated as Cpd A) concurrently or sequentially with cholestyramine (abbreviated as CHO).

As used herein, miRNA122, also abbreviated as miR122 and also known as micro-RNA122, is a microRNA that is highly expressed in the liver and may be considered as a biomarker for liver injury. In one study, it was found that some animals showed minimal to moderate increases in miR122 compared to respective controls, which after co-treatment with cholestyramine followed a trend towards decreased miR122 level (see FIG. 2).

Thus, in one embodiment, the invention relates to a method of reducing levels of miR122 in a patient receiving FGFR4 inhibition therapy, comprising administering to said patient a pharmaceutical combination comprising an FGFR4 inhibitor and a bile acid sequestrant. Thus, the present invention offers the possibility to continue valuable treatment with FGFR4 inhibitors while mitigating or reversing side effects associated with said treatment.

In another embodiment, the invention relates to a method for diminishing the incidence or severity of liver enzyme elevation during FGFR4 inhibition therapy comprising administering to a subject in need of FGFR4 inhibition therapy a combination comprising the simultaneous or sequential administration of a therapeutically effective amount of an FGFR4 inhibitor and a therapeutically effective amount of a bile acid sequestrant, wherein the incidence or severity of liver enzyme elevation during FGFR4 inhibition therapy is diminished.

In another embodiment, the invention relates to a method for lowering the level of liver enzyme in the serum of a subject on FGFR4 inhibition therapy comprising administering to the subject an amount of bile acid sequestrant effective to lower the level of liver enzyme.

In another embodiment, the invention relates to a method for lowering the level of miRNA122 in a subject on FGFR4 inhibition therapy comprising administering to the subject an amount of bile acid sequestrant effective to lower the level of miRNA122.

Bile acid sequestrants are marketed as single drugs and so their dosage and mode of administration can be in accordance with the information provided on the package insert of said bile acid sequestrant, if not mentioned herein otherwise.

The optimal dosage of each combination partner for use as a medicament according to the invention can be determined empirically for each subject using known methods and will depend upon a variety of factors, including, though not limited to, the degree of advancement of the disease; the age, body weight, general health, gender and diet of the subject; the time and route of administration; and other medications the individual is taking. Frequency of dosage may vary depending on the compound used and the particular condition to be treated or prevented. In general, the use of the minimum dosage that is sufficient to provide effective therapy is preferred. Subjects may generally be monitored for therapeutic effectiveness using assays suitable for the condition being treated or prevented, which will be familiar to those of ordinary skill in the art. Subjects may also generally be monitored for the effectiveness at reducing or preventing liver enzyme elevation using tests routinely used in the field.

Thus, in another aspect, the invention relates to a therapeutic regimen comprising the simultaneous or sequential administration of an FGFR4 inhibitor and a bile acid sequestrant. In an embodiment, the FGFR4 inhibitor is a compound of formula (I) as described in WO2015059668. In a preferred embodiment, the FGFR4 inhibitor is N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form.

In an embodiment, the bile acid sequestrant used in the therapeutic regimen of the invention is cholestyramine.

In another embodiment, the therapeutic regimen is for the treatment of a disease treatable by FGFR4 inhibition. In an embodiment, the disease is selected from liver cancer, breast cancer, glioblastoma, prostate cancer, rhabdomyosarcoma, gastric cancer, ovarian cancer, lung cancer, colon cancer. In a preferred embodiment, the disease is liver cancer.

Various embodiments of the invention are described herein. It will be recognized that features specified in each embodiment may be combined with other specified features to provide further embodiments of the present invention.

Embodiment 1

A pharmaceutical combination comprising an FGFR4 inhibitor and a bile acid sequestrant.

Embodiment 2

The pharmaceutical combination according to embodiment 1, wherein the FGFR4 inhibitor is a compound of formula (I) in free form or in pharmaceutically acceptable salt form

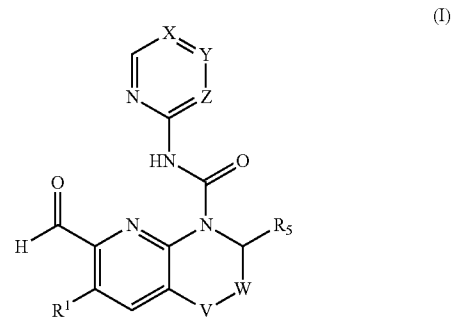

wherein
V is selected from $CH_2$, O, CH(OH);
W is selected from $CH_2$, $CH_2CH_2$, bond;
X is $C(R^X)$ or N;
Y is $C(R^Y)$ or N;
Z is CH or N;
wherein when X is N, Y and Z are not N;
wherein when Y is N, X and Z are not N;
wherein when Z is N, X and Y are not N;
$R^X$ is selected from hydrogen, halogen, halo$C_1$-$C_3$alkyl, cyano, $C_1$-$C_8$alkyl, hydroxy$C_1$-$C_8$alkyl;
$R^Y$ is selected from hydrogen, halogen, $C_1$-$C_3$alkyl, $C_1$-$C_8$alkoxy, hydroxy$C_1$-$C_3$alkoxy, $NR^{Y1}R^{Y2}$, cyano, $C_1$-$C_3$alkoxy$C_1$-$C_3$alkoxy, $C_1$-$C_3$alkoxy-halo$C_1$-$C_3$alkoxy, di($C_1$-$C_3$alkyl)amino$C_1$-$C_8$alkoxy, O—$(CH_2)_{0-1}$—$R^{Y3}$, $CR^{Y6}R^{Y7}$, S—$C_1$-$C_3$alkyl, halo$C_1$-$C_8$alkoxy optionally substituted with hydroxy;
or
$R^X$ and $R^Y$ together with the ring to which they are attached form a bicyclic aromatic ring system optionally further comprising one or two heteroatoms selected from N, O, or S, which ring system is optionally substituted with $C_1$-$C_3$alkyl;
$R^{Y1}$ is hydrogen and
$R^{Y2}$ is selected from $C_1$-$C_8$alkyl; hydroxy$C_1$-$C_8$alkyl; halo$C_1$-$C_8$alkyl optionally substituted with hydroxy; $C_1$-$C_4$alkoxy$C_1$-$C_8$alkyl; halo$C_1$-$C_3$alkoxy$C_1$-$C_8$alkyl; $(CH_2)_{0-1}$—$R^{Y4}$; di($C_1$-$C_3$alkyl)amino$C_1$-$C_8$alkyl substituted with hydroxy; bicyclo$C_5$-$C_8$alkyl optionally substituted with hydroxy$C_1$-$C_3$alkyl; phenyl substituted with $S(O)_2$—$CH(CH_3)_2$; $C_2$-$C_3$alkylsulfonic acid;
or
$R^{Y1}$ and $R^{Y2}$ together with the N atom to which they are attached form a saturated or unsaturated non-aromatic 6-membered heterocyclic ring which may contain an O atom, which ring may be substituted once or twice by $R^{Y5}$;
$R^{Y3}$ is selected from quinuclidinyl, a 4-, 5- or 6-membered saturated heterocyclic ring comprising at least one heteroatom selected from N, O or S, or a 5- or 6-membered aromatic heterocyclic ring, which saturated or aromatic heterocyclic ring is optionally substituted with $C_1$-$C_3$alkyl and/or oxo;

$R^{Y4}$ is a 4-, 5- or 6-membered saturated heterocyclic ring comprising at least one heteroatom selected from N, O, or S, which ring is optionally substituted with $C_1$-$C_3$alkyl; $R^{Y5}$ is independently selected from $C_1$-$C_3$alkyl, hydroxy, di($C_1$-$C_3$alkyl)amino$C_1$-$C_3$alkyl, or two $R^{Y5}$ attached at the same carbon atom form together with the carbon atom to which they are attached a 5-membered saturated heterocyclic ring comprising at least one heteroatom selected from N, O or S, which ring is substituted once or more than once with $C_1$-$C_3$alkyl;

$R^{Y6}$ and $R^{Y7}$ together with the carbon atom to which they are attached form a 6-membered saturated or unsaturated non-aromatic heterocyclic ring comprising one heteroatom selected from N, O or S;

$R^1$ is selected from hydrogen; halogen; $C_1$-$C_3$alkyl; halo$C_1$-$C_3$alkyl; hydroxy$C_1$-$C_3$alkyl; $C_3$-$C_6$cycloalkyl; $CH_2NR^2R^3$; $CH(CH_3)NR^2R^3$; $C_1$-$C_3$alkoxy$C_1$-$C_3$alkyl; $CH_2CO_2H$; $C(O)H$; $C_1$-$C_3$alkoxy; a 5- or 6-membered saturated heterocyclic or aromatic heterocyclic ring comprising at least one heteroatom selected from N, O or S, which ring is optionally substituted once or more than once with a group independently selected from $C_1$-$C_3$alkyl, halo$C_1$-$C_3$alkyl, oxetanyl or oxo;

$R^2$ is selected from $C_1$-$C_3$alkyl, di($C_1$-$C_3$alkyl)amino$C_1$-$C_3$alkyl;

$R^3$ is selected from $C_1$-$C_3$alkyl, $C(O)C_1$-$C_3$alkyl, $C(O)$—$CH_2$—OH, $C(O)$—$CH_2$—O—$CH_3$, $C(O)$—$CH_2$—N($CH_3$)$_2$, $S(O)_2CH_3$;

or $R^2$ and $R^3$ together with the N atom to which they are attached form a saturated 5- or 6-membered ring optionally comprising one additional heteroatom selected from N, N-oxide, O or S, which ring may be substituted once or more than once with $R^4$;

$R^4$ is independently selected from $C_1$-$C_3$alkyl, di($C_1$-$C_3$alkyl)amino, $C(O)CH_3$, hydroxy;

or two $R^4$ attached at the same carbon atom form together with the carbon atom to which they are attached a 4-, 5- or 6-membered non-aromatic heterocyclic ring comprising at least one heteroatom selected from N, O or S;

or two $R^4$ attached at the same ring atom form an oxo group;

$R^5$ is selected from hydrogen or $C_1$-$C_3$alkyl.

Embodiment 3

The pharmaceutical combination according to embodiment 1 or 2, wherein the FGFR4 inhibitor is selected from 7-formyl-N-(5-(trifluoromethyl)pyridin-2-yl)-3,4-dihydro-1,8-naphthyridine-1(2H)-carboxamide;

N-(4,5-dichloropyridin-2-yl)-7-formyl-3,4-dihydro-1,8-naphthyridine-1(2H)-carboxamide;

N-(5-cyanopyridin-2-yl)-7-formyl-3,4-dihydro-1,8-naphthyridine-1(2H)-carboxamide;

N-(5-chloropyridin-2-yl)-7-formyl-3,4-dihydro-1,8-naphthyridine-1(2H)-carboxamide;

7-formyl-N-(pyridin-2-yl)-3,4-dihydro-1,8-naphthyridine-1(2H)-carboxamide;

N-(4,5-dimethylpyridin-2-yl)-7-formyl-3,4-dihydro-1,8-naphthyridine-1(2H)-carboxamide;

7-formyl-N-(5-methylpyridin-2-yl)-3,4-dihydro-1,8-naphthyridine-1(2H)-carboxamide;

N-(5-cyanopyrimidin-2-yl)-7-formyl-3,4-dihydro-1,8-naphthyridine-1(2H)-carboxamide;

6-formyl-N-(5-methylpyridin-2-yl)-2H-pyrido[3,2-b][1,4]oxazine-4(3H)-carboxamide;

6-chloro-N-(5-cyanopyridin-2-yl)-7-formyl-3,4-dihydro-1,8-naphthyridine-1(2H)-carboxamide;

7-formyl-N-(6-methoxypyrimidin-4-yl)-3,4-dihydro-1,8-naphthyridine-1(2H)-carboxamide;

N-(5-cyanopyrazin-2-yl)-7-formyl-3,4-dihydro-1,8-naphthyridine-1(2H)-carboxamide;

N-(5-cyano-4-methoxypyridin-2-yl)-7-formyl-3,4-dihydro-1,8-naphthyridine-1(2H)-carboxamide;

6-formyl-N-(5-(trifluoromethyl)pyridin-2-yl)-2H-pyrido[3,2-b][1,4]oxazine-4(3H)-carboxamide;

6-fluoro-7-formyl-N-(5-(trifluoromethyl)pyridin-2-yl)-3,4-dihydro-1,8-naphthyridine-1(2H)-carboxamide;

N-(5-chloro-4-((2-(isopropylsulfonyl)phenyl)amino)pyrimidin-2-yl)-7-formyl-3,4-dihydro-1,8-naphthyridine-1(2H)-carboxamide;

N-(4,5-dicyanopyridin-2-yl)-7-formyl-3,4-dihydro-1,8-naphthyridine-1(2H)-carboxamide;

7-formyl-6-(hydroxymethyl)-N-(5-(trifluoromethyl)pyridin-2-yl)-3,4-dihydro-1,8-naphthyridine-1(2H)-carboxamide;

N-(5-cyano-4-ethoxypyridin-2-yl)-7-formyl-3,4-dihydro-1,8-naphthyridine-1(2H)-carboxamide;

7-formyl-6-methyl-N-(5-(trifluoromethyl)pyridin-2-yl)-3,4-dihydro-1,8-naphthyridine-1(2H)-carboxamide;

N-(5-cyanopyridin-2-yl)-7-formyl-6-methyl-3,4-dihydro-1,8-naphthyridine-1(2H)-carboxamide;

7-formyl-N-(5-(1-hydroxypentyl)pyridin-2-yl)-3,4-dihydro-1,8-naphthyridine-1(2H)-carboxamide;

N-(5-cyano-4-(2-methoxyethoxy)pyridin-2-yl)-7-formyl-3,4-dihydro-1,8-naphthyridine-1(2H)-carboxamide;

N-(4-chloro-5-cyanopyridin-2-yl)-7-formyl-3,4-dihydro-1,8-naphthyridine-1(2H)-carboxamide;

N-(5-cyano-4-morpholinopyridin-2-yl)-7-formyl-3,4-dihydro-1,8-naphthyridine-1(2H)-carboxamide;

N-(5-cyano-4-(4-hydroxy-4-methylpiperidin-1-yl)pyridin-2-yl)-7-formyl-3,4-dihydro-1,8-naphthyridine-1(2H)-carboxamide;

N-(5-cyanopyridin-2-yl)-7-formyl-6-(hydroxymethyl)-3,4-dihydro-1,8-naphthyridine-1(2H)-carboxamide;

N-(5-cyano-4-(2-methyl-2,8-diazaspiro[4.5]decan-8-yl)pyridin-2-yl)-7-formyl-3,4-dihydro-1,8-naphthyridine-1(2H)-carboxamide;

N-(5-cyanopyridin-2-yl)-6-cyclopropyl-7-formyl-3,4-dihydro-1,8-naphthyridine-1(2H)-carboxamide;

N-(5-cyano-4-(3,6-dihydro-2H-pyran-4-yl)pyridin-2-yl)-7-formyl-3,4-dihydro-1,8-naphthyridine-1(2H)-carboxamide;

N-(5-cyano-4-(tetrahydro-2H-pyran-4-yl)pyridin-2-yl)-7-formyl-3,4-dihydro-1,8-naphthyridine-1(2H)-carboxamide;

N-(5-chloro-4-((tetrahydrofuran-3-yl)oxy)pyrimidin-2-yl)-7-formyl-3,4-dihydro-1,8-naphthyridine-1(2H)-carboxamide;

N-(5-cyano-4-isopropoxypyridin-2-yl)-7-formyl-3,4-dihydro-1,8-naphthyridine-1(2H)-carboxamide;

N-(5-cyano-4-((tetrahydrofuran-2-yl)methoxy)pyridin-2-yl)-7-formyl-3,4-dihydro-1,8-naphthyridine-1(2H)-carboxamide;

N-(5-cyano-4-(oxetan-2-ylmethoxy)pyridin-2-yl)-7-formyl-3,4-dihydro-1,8-naphthyridine-1(2H)-carboxamide;

N-(5-cyano-4-((tetrahydro-2H-pyran-2-yl)methoxy)pyridin-2-yl)-7-formyl-3,4-dihydro-1,8-naphthyridine-1(2H)-carboxamide;

N-(5-cyanopyridin-2-yl)-6-(difluoromethyl)-7-formyl-3,4-dihydro-1,8-naphthyridine-1(2H)-carboxamide;

N-(5-cyano-4-(2-(dimethylamino)ethoxy)pyridin-2-yl)-7-formyl-3,4-dihydro-1,8-naphthyridine-1(2H)-carboxamide;

N-(5-cyano-4-(2-methoxyethoxy)pyridin-2-yl)-7-formyl-6-(hydroxymethyl)-3,4-dihydro-1,8-naphthyridine-1(2H)-carboxamide;

N-(5-cyano-4-((tetrahydrofuran-3-yl)oxy)pyridin-2-yl)-7-formyl-3,4-dihydro-1,8-naphthyridine-1(2H)-carboxamide;

N-(5-cyano-4-(4-hydroxy-4-methylpiperidin-1-yl)pyridin-2-yl)-7-formyl-6-(hydroxymethyl)-3,4-dihydro-1,8-naphthyridine-1(2H)-carboxamide;

7-acetyl-N-(5-cyanopyridin-2-yl)-6-((dimethylamino)methyl)-3,4-dihydro-1,8-naphthyridine-1(2H)-carboxamide;

N-(5-cyano-4-((tetrahydrofuran-2-yl)methoxy)pyridin-2-yl)-7-formyl-6-(hydroxymethyl)-3,4-dihydro-1,8-naphthyridine-1(2H)-carboxamide;

N-(5-cyano-4-((tetrahydro-2H-pyran-2-yl)methoxy)pyridin-2-yl)-7-formyl-6-(hydroxymethyl)-3,4-dihydro-1,8-naphthyridine-1(2H)-carboxamide;

N-(5-cyano-4-(2-methyl-2,8-diazaspiro[4.5]decan-8-yl)pyridin-2-yl)-7-formyl-6-(hydroxymethyl)-3,4-dihydro-1,8-naphthyridine-1(2H)-carboxamide;

N-(5-cyano-4-((1-methyl pyrrolidin-3-yl)oxy)pyridin-2-yl)-7-formyl-6-(hydroxymethyl)-3,4-dihydro-1,8-naphthyridine-1(2H)-carboxamide;

N-(5-cyano-4-((1-methylpiperidin-4-yl)oxy)pyridin-2-yl)-7-formyl-6-(hydroxymethyl)-3,4-dihydro-1,8-naphthyridine-1(2H)-carboxamide;

N-(5-cyano-4-((1-methoxypropan-2-yl)oxy)pyridin-2-yl)-7-formyl-6-(hydroxymethyl)-3,4-dihydro-1,8-naphthyridine-1(2H)-carboxamide;

N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide;

N-(5-cyano-4-((tetrahydrofuran-3-yl)oxy)pyridin-2-yl)-6-((dimethylamino)methyl)-7-formyl-3,4-dihydro-1,8-naphthyridine-1(2H)-carboxamide;

2-(8-((5-cyanopyridin-2-yl)carbamoyl)-2-formyl-5,6,7,8-tetrahydro-1,8-naphthyridin-3-yl)acetic acid;

N-(5-cyano-4-((tetrahydro-2H-pyran-4-yl)oxy)pyridin-2-yl)-7-formyl-6-(hydroxymethyl)-3,4-dihydro-1,8-naphthyridine-1(2H)-carboxamide;

N-(5-cyano-4-((1-methyl pyrrolidin-3-yl)oxy)pyridin-2-yl)-7-formyl-6-(hydroxymethyl)-3,4-dihydro-1,8-naphthyridine-1(2H)-carboxamide;

N-(5-cyano-4-(((tetrahydro-2H-pyran-3-yl)methyl)amino)pyridin-2-yl)-7-formyl-6-(hydroxymethyl)-3,4-dihydro-1,8-naphthyridine-1(2H)-carboxamide;

N-(5-cyano-4-((tetrahydrofuran-3-yl)amino)pyridin-2-yl)-7-formyl-6-(hydroxymethyl)-3,4-dihydro-1,8-naphthyridine-1(2H)-carboxamide;

N-(5-cyano-4-((2-methoxypropyl)amino)pyridin-2-yl)-7-formyl-6-(hydroxymethyl)-3,4-dihydro-1,8-naphthyridine-1(2H)-carboxamide;

N-(5-chloro-44(1-methoxypropan-2-yl)oxy)pyrimidin-2-yl)-7-formyl-6-(hydroxymethyl)-3,4-dihydro-1,8-naphthyridine-1(2H)-carboxamide;

N-(4-(4-chloro-2-hydroxybutoxy)-5-cyanopyridin-2-yl)-7-formyl-6-(hydroxymethyl)-3,4-dihydro-1,8-naphthyridine-1(2H)-carboxamide;

N-(5-cyano-4-(2-methoxyethoxy)pyridin-2-yl)-7-formyl-6-(trifluoromethyl)-3,4-dihydro-1,8-naphthyridine-1(2H)-carboxamide;

N-(5-cyano-4-(2-methoxyethoxy)pyridin-2-yl)-6-cyclopropyl-7-formyl-3,4-dihydro-1,8-naphthyridine-1(2H)-carboxamide;

N-(5-cyano-4-(2-methoxyethoxy)pyridin-2-yl)-6-(difluoromethyl)-7-formyl-3,4-dihydro-1,8-naphthyridine-1(2H)-carboxamide;

N-(5-cyano-4-(2-methoxyethoxy)pyridin-2-yl)-6-((dimethylamino)methyl)-7-formyl-3,4-dihydro-1,8-naphthyridine-1(2H)-carboxamide;

N-(5-cyano-4-((3-(hydroxymethyl)bicyclo[2.2.1]heptan-2-yl)amino)pyridin-2-yl)-7-formyl-6-(hydroxymethyl)-3,4-dihydro-1,8-naphthyridine-1(2H)-carboxamide;

N-(5-cyano-4-((tetrahydro-2H-pyran-4-yl)amino)pyridin-2-yl)-7-formyl-6-(hydroxymethyl)-3,4-dihydro-1,8-naphthyridine-1(2H)-carboxamide;

N-(5-cyano-4-(2-m ethoxyethoxy)pyridin-2-yl)-7-formyl-6-(methoxymethyl)-3,4-dihydro-1,8-naphthyridine-1(2H)-carboxamide;

N-(5-cyanopyridin-2-yl)-7-formyl-6-((N-methylacetamido)methyl)-3,4-dihydro-1,8-naphthyridine-1(2H)-carboxamide;

N-(5-chloro-4-((tetrahydrofuran-3-yl)oxy)pyrimidin-2-yl)-7-formyl-6-(hydroxymethyl)-3,4-dihydro-1,8-naphthyridine-1(2H)-carboxamide;

N-(5-cyano-4-((tetrahydrofuran-3-yl)oxy)pyrimidin-2-yl)-7-formyl-6-(hydroxymethyl)-3,4-dihydro-1,8-naphthyridine-1(2H)-carboxamide;

7-formyl-6-(hydroxymethyl)-N-(4-((tetrahydrofuran-3-yl)oxy)pyridin-2-yl)-3,4-dihydro-1,8-naphthyridine-1(2H)-carboxamide;

N-(5-chloro-4-((tetrahydrofuran-3-yl)oxy)pyridin-2-yl)-7-formyl-6-(hydroxymethyl)-3,4-dihydro-1,8-naphthyridine-1(2H)-carboxamide;

N-(5-cyano-4-((1-methylpiperidin-3-yl)methoxy)pyridin-2-yl)-7-formyl-6-(hydroxymethyl)-3,4-dihydro-1,8-naphthyridine-1(2H)-carboxamide;

N-(5-cyano-4-((1-methyl pyrrolidin-2-yl)methoxy)pyridin-2-yl)-7-formyl-6-(hydroxymethyl)-3,4-dihydro-1,8-naphthyridine-1(2H)-carboxamide;

N-(5-cyano-4-((1-methylpiperidin-2-yl)methoxy)pyridin-2-yl)-7-formyl-6-(hydroxymethyl)-3,4-dihydro-1,8-naphthyridine-1(2H)-carboxamide;

N-(5-fluoropyridin-2-yl)-7-formyl-6-(hydroxymethyl)-3,4-dihydro-1,8-naphthyridine-1(2H)-carboxamide;

N-(5-cyano-4-(2-(dimethylamino)ethoxy)pyridin-2-yl)-6-form-$^{13}$C-yl-2H-pyrido[3,2-b][1,4]oxazine-4(3H)-carboxamide;

N-(5-cyano-4-((1-methylpiperidin-4-yl)methoxy)pyridin-2-yl)-7-formyl-6-(hydroxymethyl)-3,4-dihydro-1,8-naphthyridine-1(2H)-carboxamide;

N-(5-cyanopyridin-2-yl)-7-formyl-4-hydroxy-3,4-dihydro-1,8-naphthyridine-1(2H)-carboxamide;

N-(5-cyano-4-((2-methoxyethyl)amino)pyridin-2-yl)-7-formyl-6-(hydroxymethyl)-3,4-dihydro-1,8-naphthyridine-1(2H)-carboxamide;

N-(5-cyano-4-(2-((dimethylamino)methyl)morpholino)pyridin-2-yl)-7-formyl-6-(hydroxymethyl)-3,4-dihydro-1,8-naphthyridine-1(2H)-carboxamide;

N-(5-cyano-4-(quinuclidin-3-yloxy)pyridin-2-yl)-7-formyl-6-(hydroxymethyl)-3,4-dihydro-1,8-naphthyridine-1(2H)-carboxamide;

N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide;

7-formyl-6-(hydroxymethyl)-N-(44(2-methoxyethyl)amino)-5-(trifluoromethyl)pyridin-2-yl)-3,4-dihydro-1,8-naphthyridine-1(2H)-carboxamide;

N-(5-cyano-4-(4-((dimethylamino)methyl)-4-hydroxypiperidin-1-yl)pyridin-2-yl)-7-formyl-6-(hydroxymethyl)-3,4-dihydro-1,8-naphthyridine-1(2H)-carboxamide;

N-(5-cyano-4-((2-hydroxy-2-methylpropyl)amino)pyridin-2-yl)-7-formyl-6-(hydroxymethyl)-3,4-dihydro-1,8-naphthyridine-1(2H)-carboxamide;

N-(5-cyano-4-((3-(dimethylamino)-2-hydroxy-2-methylpropyl)amino)pyridin-2-yl)-7-formyl-6-(hydroxymethyl)-3,4-dihydro-1,8-naphthyridine-1(2H)-carboxamide;

N-(5-cyano-4-((2-fluoroethyl)amino)pyridin-2-yl)-7-formyl-6-(hydroxymethyl)-3,4-dihydro-1,8-naphthyridine-1(2H)-carboxamide;

N-(5-cyano-4-(2,2,2-trifluoroethoxy)pyridin-2-yl)-7-formyl-6-(hydroxymethyl)-3,4-dihydro-1,8-naphthyridine-1(2H)-carboxamide;

N-(5-cyano-4-isopropoxypyridin-2-yl)-7-formyl-6-((4-methyl-2-oxopiperazin-1-yl)methyl)-3,4-dihydro-1,8-naphthyridine-1(2H)-carboxamide;

N-(5-cyano-4-(isopropylamino)pyridin-2-yl)-7-formyl-6-((4-methyl-2-oxopiperazin-1-yl)methyl)-3,4-dihydro-1,8-naphthyridine-1(2H)-carboxamide;

N-(5-cyano-4-((2-methoxyethyl)amino)pyridin-2-yl)-7-formyl-6-((3-oxomorpholino)methyl)-3,4-dihydro-1,8-naphthyridine-1(2H)-carboxamide;

N-(5-cyano-4-((2-methoxyethyl)amino)pyridin-2-yl)-7-formyl-6-((3-hydroxy-2-oxopyrrolidin-1-yl)methyl)-3,4-dihydro-1,8-naphthyridine-1(2H)-carboxamide;

N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide;

N-(5-cyano-4-ethylpyridin-2-yl)-6,7-diformyl-3,4-dihydro-1,8-naphthyridine-1(2H)-carboxamide;

N-(5-cyano-4-((2-methoxyethyl)amino)pyridin-2-yl)-7-formyl-6-((2-oxopiperazin-1-yl)methyl)-3,4-dihydro-1,8-naphthyridine-1(2H)-carboxamide hydrochloride;

N-(5-cyano-4-((1-methoxypropan-2-yl)oxy)pyridin-2-yl)-7-formyl-6-((4-methyl-2-oxooxazolidin-3-yl)methyl)-3,4-dihydro-1,8-naphthyridine-1(2H)-carboxamide;

N-(5-cyano-4-((2-methoxyethyl)amino)pyridin-2-yl)-7-formyl-6-((3-methyl-5-oxomorpholino)methyl)-3,4-dihydro-1,8-naphthyridine-1(2H)-carboxamide;

6-((4-acetyl piperazin-1-yl)methyl)-N-(5-cyano-4-isopropoxypyridin-2-yl)-7-formyl-3,4-dihydro-1,8-naphthyridine-1(2H)-carboxamide;

N-(5-cyano-4-((2-methoxyethyl)amino)pyridin-2-yl)-7-formyl-6-(1-(N-methylacetamido)ethyl)-3,4-dihydro-1,8-naphthyridine-1(2H)-carboxamide;

N-(5-cyano-4-isopropoxypyridin-2-yl)-7-formyl-6-((2-hydroxy-N-methylacetamido)methyl)-3,4-dihydro-1,8-naphthyridine-1(2H)-carboxamide;

N-(5-cyano-4-((2-methoxyethyl)amino)pyridin-2-yl)-6-((N-(2-(dimethylamino)ethyl)acetamido)methyl)-7-formyl-3,4-dihydro-1,8-naphthyridine-1(2H)-carboxamide;

N-(5-cyano-4-((2-methoxyethyl)amino)pyridin-2-yl)-6-((N-(2-(dimethylamino)ethyl)methylsulfonamido)methyl)-7-formyl-3,4-dihydro-1,8-naphthyridine-1(2H)-carboxamide;

N-(5-cyano-4-isopropoxypyridin-2-yl)-6-((2-(dimethylamino)-N-methylacetamido)methyl)-7-formyl-3,4-dihydro-1,8-naphthyridine-1(2H)-carboxamide;

N-(5-cyano-4-((2-methoxyethyl)amino)pyridin-2-yl)-7-formyl-6-((2-methoxy-N-methylacetamido)methyl)-3,4-dihydro-1,8-naphthyridine-1(2H)-carboxamide;

N-(5-cyano-4-((2-methoxyethyl)amino)pyridin-2-yl)-7-formyl-6-((3-oxothiomorpholino)methyl)-3,4-dihydro-1,8-naphthyridine-1(2H)-carboxamide;

N-(5-cyano-4-((2-methoxyethyl)amino)pyridin-2-yl)-6-((1,1-dioxido-3-oxothiomorpholino)methyl)-7-formyl-3,4-dihydro-1,8-naphthyridine-1(2H)-carboxamide;

N-(5-cyano-4-(((4-methylmorpholin-2-yl)methyl)amino)pyridin-2-yl)-6-(difluoromethyl)-7-formyl-3,4-dihydro-1,8-naphthyridine-1(2H)-carboxamide;

N-(5-cyano-4-((1,1,1-trifluoro-3-methoxypropan-2-yl)oxy)pyridin-2-yl)-6-(difluoromethyl)-7-formyl-3,4-dihydro-1,8-naphthyridine-1(2H)-carboxamide;

N-(5-cyano-4-((2-(trifluoromethoxy)ethyl)amino)pyridin-2-yl)-7-formyl-6-((N-methylacetamido)methyl)-3,4-dihydro-1,8-naphthyridine-1(2H)-carboxamide;

6-(2-oxa-5-azaspiro[3.4]octan-5-ylmethyl)-N-(5-cyano-4-((2-methoxyethyl)amino)pyridin-2-yl)-7-formyl-3,4-dihydro-1,8-naphthyridine-1(2H)-carboxamide;

N-(4-((2-(tert-butoxy)ethyl)amino)-5-cyanopyridin-2-yl)-7-formyl-6-((4-methyl-2-oxopiperazin-1-yl)methyl)-3,4-dihydro-1,8-naphthyridine-1(2H)-carboxamide;

N-(5-cyano-4-((2-hydroxyethyl)amino)pyridin-2-yl)-7-formyl-6-((4-methyl-2-oxopiperazin-1-yl)methyl)-3,4-dihydro-1,8-naphthyridine-1(2H)-carboxamide;

N-(5-cyano-4-(2-hydroxyethoxy)pyridin-2-yl)-7-formyl-6-((4-methyl-2-oxopiperazin-1-yl)methyl)-3,4-dihydro-1,8-naphthyridine-1(2H)-carboxamide;

N-(5-cyanopyridin-2-yl)-2-formyl-7,8-dihydro-5H-pyrido[2,3-b]azepine-9(6H)-carboxamide;

N-(5-cyano-4-(2-methoxyethoxy)pyridin-2-yl)-2-formyl-7,8-dihydro-5H-pyrido[2,3-b]azepine-9(6H)-carboxamide;

N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide;

7-formyl-N-(1-isopropyl-1H-imidazo[4,5-c]pyridin-6-yl)-6-((4-methyl-2-oxopiperazin-1-yl)methyl)-3,4-dihydro-1,8-naphthyridine-1(2H)-carboxamide;

7-formyl-N-(1-isopropyl-1H-imidazo[4,5-c]pyridin-6-yl)-6-((2-oxopyrrolidin-1-yl)methyl)-3,4-dihydro-1,8-naphthyridine-1(2H)-carboxamide;

4-((8-((5-cyano-4-((2-methoxyethyl)amino)pyridin-2-yl)carbamoyl)-2-formyl-5,6,7,8-tetrahydro-1,8-naphthyridin-3-yl)methyl)-1-methyl-3-oxopiperazine 1-oxide;

N-(5-cyano-4-((2-oxopiperidin-4-yl)methoxy)pyridin-2-yl)-7-formyl-6-((2-oxopyrrolidin-1-yl)methyl)-3,4-dihydro-1,8-naphthyridine-1(2H)-carboxamide;

N-(5-cyano-4-(2-methoxyethoxy)pyridin-2-yl)-7-formyl-2-methyl-6-((4-methyl-2-oxopiperazin-1-yl)methyl)-3,4-dihydro-1,8-naphthyridine-1(2H)-carboxamide;

N-(5-cyano-4-isopropoxypyridin-2-yl)-7-formyl-2-methyl-6-((4-methyl-2-oxopiperazin-1-yl)methyl)-3,4-dihydro-1,8-naphthyridine-1(2H)-carboxamide;

N-(5-cyano-4-((2-methoxyethyl)amino)pyridin-2-yl)-7-formyl-2-methyl-6-((4-methyl-2-oxopiperazin-1-yl)methyl)-3,4-dihydro-1,8-naphthyridine-1(2H)-carboxamide;

N-(5-cyano-4-((2-methoxyethyl)amino)pyridin-2-yl)-7-formyl-6-((3-hydroxy-4-methyl-2-oxopiperazin-1-yl)methyl)-3,4-dihydro-1,8-naphthyridine-1(2H)-carboxamide;

N-(5-cyano-4-isopropoxypyridin-2-yl)-6-formyl-2,3-dihydro-1H-pyrrolo[2,3-b]pyridine-1-carboxamide;

2-((5-cyano-2-(7-formyl-6-((4-methyl-2-oxopiperazin-1-yl)methyl)-1,2,3,4-tetrahydro-1,8-naphthyridine-1-carboxamido)pyridin-4-yl)amino)ethyl hydrogen sulfate;

N-(4-(bicyclo[1.1.1]pentan-1-ylamino)-5-cyanopyridin-2-yl)-7-formyl-6-((4-methyl-2-oxopiperazin-1-yl)methyl)-3,4-dihydro-1,8-naphthyridine-1(2H)-carboxamide;

N-(5-cyano-4-(thiophen-2-ylmethoxy)pyridin-2-yl)-7-formyl-6-((N-methylacetamido)methyl)-3,4-dihydro-1,8-naphthyridine-1(2H)-carboxamide;
N-(5-cyano-4-(isopropylthio)pyridin-2-yl)-7-formyl-6-((N-methylacetamido)methyl)-3,4-dihydro-1,8-naphthyridine-1(2H)-carboxamide;
N-(5-cyano-4-((2-methoxyethyl)amino)pyridin-2-yl)-6-((3,5-dimethylpiperazin-1-yl)methyl)-7-formyl-3,4-dihydro-1,8-naphthyridine-1(2H)-carboxamide;
N-(5-cyano-4-((2-methoxyethyl)amino)pyridin-2-yl)-7-formyl-6-((3,3,4-trimethyl-2-oxopiperazin-1-yl)methyl)-3,4-dihydro-1,8-naphthyridine-1(2H)-carboxamide;
6-amino-N-(5-cyanopyridin-2-yl)-7-formyl-3,4-dihydro-1,8-naphthyridine-1(2H)-carboxamide;
N-(5-cyano-4-((2-methoxyethyl)amino)pyridin-2-yl)-7-formyl-6-(tetrahydro-2H-pyran-4-yl)-3,4-dihydro-1,8-naphthyridine-1(2H)-carboxamide;
N-(5-cyano-4-((2-methoxyethyl)amino)pyridin-2-yl)-6-(1,3-dimethyl-1H-pyrazol-4-yl)-7-formyl-3,4-dihydro-1,8-naphthyridine-1(2H)-carboxamide;
N-(5-cyano-4-((2-methoxyethyl)amino)pyridin-2-yl)-7-formyl-6-(1-methyl-1H-pyrazol-4-yl)-3,4-dihydro-1,8-naphthyridine-1(2H)-carboxamide;
N-(5-cyano-4-((2-methoxyethyl)amino)pyridin-2-yl)-7-formyl-6-(2-methylthiazol-5-yl)-3,4-dihydro-1,8-naphthyridine-1(2H)-carboxamide;
N-(5-cyano-4-((2-methoxyethyl)amino)pyridin-2-yl)-7-formyl-6-(thiophen-2-yl)-3,4-dihydro-1,8-naphthyridine-1(2H)-carboxamide;
N-(5-cyano-4-((2-methoxyethyl)amino)pyridin-2-yl)-7-formyl-6-(1H-imidazol-1-yl)-3,4-dihydro-1,8-naphthyridine-1(2H)-carboxamide;
N-(5-cyano-4-((2-methoxyethyl)amino)pyridin-2-yl)-7-formyl-6-(pyridin-3-yl)-3,4-dihydro-1,8-naphthyridine-1(2H)-carboxamide;
N-(5-cyano-4-((2-methoxyethyl)amino)pyridin-2-yl)-7-formyl-6-(1-methyl-1H-pyrazol-5-yl)-3,4-dihydro-1,8-naphthyridine-1(2H)-carboxamide;
N-(5-cyano-4-((2-methoxyethyl)amino)pyridin-2-yl)-7-formyl-6-(3-methyl-1H-1,2,4-triazol-1-yl)-3,4-dihydro-1,8-naphthyridine-1(2H)-carboxamide;
N-(5-cyano-4-((2-methoxyethyl)amino)pyridin-2-yl)-7-formyl-6-(3-methyl-2-oxopyrrolidin-1-yl)-3,4-dihydro-1,8-naphthyridine-1(2H)-carboxamide;
N-(5-cyano-4-((2-methoxyethyl)amino)pyridin-2-yl)-7-formyl-6-(3-oxomorpholino)-3,4-dihydro-1,8-naphthyridine-1(2H)-carboxamide;
N-(5-cyano-4-((2-methoxyethyl)amino)pyridin-2-yl)-7-formyl-6-(2-oxooxazolidin-3-yl)-3,4-dihydro-1,8-naphthyridine-1(2H)-carboxamide;
N-(5-cyano-4-isopropoxypyridin-2-yl)-7-formyl-6-(tetrahydrofuran-3-yl)-3,4-dihydro-1,8-naphthyridine-1(2H)-carboxamide;
N-(5-cyano-4-isopropoxypyridin-2-yl)-7-formyl-6-(piperidin-4-yl)-3,4-dihydro-1,8-naphthyridine-1(2H)-carboxamide;
N-(5-cyano-4-((2-methoxyethyl)amino)pyridin-2-yl)-7-formyl-6-(1-(oxetan-3-yl)piperidin-4-yl)-3,4-dihydro-1,8-naphthyridine-1(2H)-carboxamide; and
N-(5-cyano-4-((2-methoxyethyl)amino)pyridin-2-yl)-6-(1-(2,2-difluoroethyl)piperidin-4-yl)-7-formyl-3,4-dihydro-1,8-naphthyridine-1(2H)-carboxamide
in free form or in pharmaceutically acceptable salt form.

Embodiment 4

The pharmaceutical combination according to any of embodiments 1 to 3, wherein the FGFR4 inhibitor is N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form.

Embodiment 5

The pharmaceutical combination according to any of embodiments 1 to 4, wherein the FGFR4 inhibitor is N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form.

Embodiment 6

The pharmaceutical combination according to any of the preceding embodiments, wherein the bile acid sequestrant is selected from cholestyramine, colesevelam, colesevalam hydrochloride, colestipol or selevamer.

Embodiment 7

The pharmaceutical combination according to embodiment 6, wherein the bile acid sequestrant is cholestyramine.

Embodiment 8

A pharmaceutical combination according to any of embodiments 1 to 7 for use as a medicament.

Embodiment 9

The pharmaceutical combination according to embodiment 8, for use in the treatment of cancer.

Embodiment 10

The pharmaceutical combination according to embodiment 8, for use in the treatment of liver cancer, breast cancer, glioblastoma, prostate cancer, rhabdomyosarcoma, gastric cancer, ovarian cancer, lung cancer, colon cancer.

Embodiment 11

The pharmaceutical combination according to embodiment 8, for use in the treatment of liver cancer.

Embodiment 12

A bile acid sequestrant for use in reducing or preventing side effects associated with FGFR4 inhibition therapy.

Embodiment 13

A bile acid sequestrant for use according to embodiment 12, wherein the side effects comprise the increase of liver enzymes in the serum, plasma or blood of a subject taking FGFR4 inhibition therapy.

Embodiment 14

A bile acid sequestrant for use according to embodiment 13, wherein the liver enzyme is alanine aminotransferase (ALT).

Embodiment 15

A bile acid sequestrant for use according to embodiment 13, wherein the liver enzyme is aspartate aminotransferase (AST).

Embodiment 16

A bile acid sequestrant for use according to embodiment 12, wherein the side effects comprise the increase of miRNA122 in a subject taking FGFR4 inhibition therapy.

Embodiment 17

A bile acid sequestrant for use according to any of embodiments 12 to 16, which is selected from cholestyramine, colesevelam, colesevalam hydrochloride, colestipol or selevamer.

Embodiment 18

A bile acid sequestrant for use according to embodiment 17, which is cholestyramine.

Embodiment 19

A pharmaceutical combination comprising a bile acid sequestrant and an FGFR4 inhibitor for use in a method for diminishing the incidence or severity of side effects associated with FGFR4 inhibition therapy which method comprises simultaneously or sequentially administering to a subject in need of FGFR4 inhibition therapy said pharmaceutical combination.

Embodiment 20

A pharmaceutical combination for use according to embodiment 19, wherein the bile acid sequestrant is selected from cholestyramine, colesevelam, colesevalam hydrochloride, colestipol or selevamer.

Embodiment 21

A pharmaceutical combination for use according to embodiment 19, wherein the bile acid sequestrant is cholestyramine.

Embodiment 22

A pharmaceutical combination for use according to any of embodiment 19 to 21, wherein the FGFR4 inhibitor is a compound of formula (I) in free form or in pharmaceutically acceptable salt form

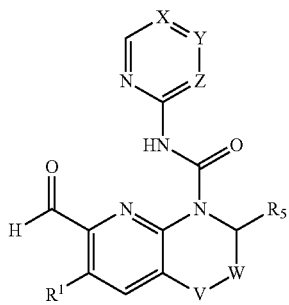

(I)

wherein
V is selected from $CH_2$, O, CH(OH);
W is selected from $CH_2$, $CH_2CH_2$, bond;
X is $C(R^X)$ or N;
Y is $C(R^Y)$ or N;
Z is CH or N;
wherein when X is N, Y and Z are not N;
wherein when Y is N, X and Z are not N;
wherein when Z is N, X and Y are not N;
$R^X$ is selected from hydrogen, halogen, halo$C_1$-$C_3$alkyl, cyano, $C_1$-$C_8$alkyl, hydroxy$C_1$-$C_8$alkyl;
$R^Y$ is selected from hydrogen, halogen, $C_1$-$C_3$alkyl, $C_1$-$C_8$alkoxy, hydroxy$C_1$-$C_3$alkoxy, $NR^{Y1}R^{Y2}$, cyano, $C_1$-$C_3$alkoxy$C_1$-$C_3$alkoxy, $C_1$-$C_3$alkoxy-halo$C_1$-$C_3$alkoxy, di($C_1$-$C_3$alkyl)amino$C_1$-$C_8$alkoxy, O—$(CH_2)_{0-1}$—$R^{Y3}$, $CR^{Y6}R^{Y7}$, S—$C_1$-$C_3$alkyl, halo$C_1$-$C_8$alkoxy optionally substituted with hydroxy;
or
$R^X$ and $R^Y$ together with the ring to which they are attached form a bicyclic aromatic ring system optionally further comprising one or two heteroatoms selected from N, O, or S, which ring system is optionally substituted with $C_1$-$C_3$alkyl;
$R^{Y1}$ is hydrogen and
$R^{Y2}$ is selected from $C_1$-$C_8$alkyl; hydroxy$C_1$-$C_8$alkyl; halo$C_1$-$C_8$alkyl optionally substituted with hydroxy; $C_1$-$C_4$alkoxy$C_1$-$C_8$alkyl; halo$C_1$-$C_3$alkoxy$C_1$-$C_8$alkyl; $(CH_2)_{0-1}$—$R^{Y4}$; di($C_1$-$C_3$alkyl)amino$C_1$-$C_8$alkyl substituted with hydroxy; bicyclo$C_5$-$C_8$alkyl optionally substituted with hydroxy$C_1$-$C_3$alkyl; phenyl substituted with $S(O)_2$—$CH(CH_3)_2$; $C_2$-$C_3$alkylsulfonic acid;
or
$R^{Y1}$ and $R^{Y2}$ together with the N atom to which they are attached form a saturated or unsaturated non-aromatic 6-membered heterocyclic ring which may contain an O atom, which ring may be substituted once or twice by $R^{Y5}$;
$R^{Y3}$ is selected from quinuclidinyl, a 4-, 5- or 6-membered saturated heterocyclic ring comprising at least one heteroatom selected from N, O or S, or a 5- or 6-membered aromatic heterocyclic ring, which saturated or aromatic heterocyclic ring is optionally substituted with $C_1$-$C_3$alkyl and/or oxo;
$R^{Y4}$ is a 4-, 5- or 6-membered saturated heterocyclic ring comprising at least one heteroatom selected from N, O, or S, which ring is optionally substituted with $C_1$-$C_3$alkyl;
$R^{Y5}$ is independently selected from $C_1$-$C_3$alkyl, hydroxy, di($C_1$-$C_3$alkyl)amino$C_1$-$C_3$alkyl,
or
two $R^{Y5}$ attached at the same carbon atom form together with the carbon atom to which they are attached a 5-membered saturated heterocyclic ring comprising at least one heteroatom selected from N, O or S, which ring is substituted once or more than once with $C_1$-$C_3$alkyl;
$R^{Y6}$ and $R^{Y7}$ together with the carbon atom to which they are attached form a 6-membered saturated or unsaturated non-aromatic heterocyclic ring comprising one heteroatom selected from N, O or S;
$R^1$ is selected from hydrogen; halogen; $C_1$-$C_3$alkyl; halo$C_1$-$C_3$alkyl; hydroxy$C_1$-$C_3$alkyl; $C_3$-$C_6$cycloalkyl; $CH_2NR^2R^3$; $CH(CH_3)NR^2R^3$; $C_1$-$C_3$alkoxy$C_1$-$C_3$alkyl; $CH_2CO_2H$; C(O)H; $C_1$-$C_3$alkoxy; a 5- or 6-membered saturated heterocyclic or aromatic heterocyclic ring comprising at least one heteroatom selected from N, O or S, which ring is optionally substituted once or more than once with a group independently selected from $C_1$-$C_3$alkyl, halo$C_1$-$C_3$alkyl, oxetanyl or oxo;

$R^2$ is selected from $C_1$-$C_3$alkyl, di($C_1$-$C_3$alkyl)amino$C_1$-$C_3$alkyl;

$R^3$ is selected from $C_1$-$C_3$alkyl, C(O)$C_1$-$C_3$alkyl, C(O)—CH$_2$—OH, C(O)—CH$_2$—O—CH$_3$, C(O)—CH$_2$—N(CH$_3$)$_2$, S(O)$_2$CH$_3$;

or $R^2$ and $R^3$ together with the N atom to which they are attached form a saturated 5- or 6-membered ring optionally comprising one additional heteroatom selected from N, N-oxide, O or S, which ring may be substituted once or more than once with $R^4$; $R^4$ is independently selected from $C_1$-$C_3$alkyl, di($C_1$-$C_3$alkyl)amino, C(O)CH$_3$, hydroxy;

or two $R^4$ attached at the same carbon atom form together with the carbon atom to which they are attached a 4-, 5- or 6-membered non-aromatic heterocyclic ring comprising at least one heteroatom selected from N, O or S;

or two $R^4$ attached at the same ring atom form an oxo group;

$R^5$ is selected from hydrogen or $C_1$-$C_3$alkyl.

Embodiment 23

A pharmaceutical combination for use according to any of embodiment 19 to 22, wherein the FGFR4 inhibitor is selected from 7-formyl-N-(5-(trifluoromethyl)pyridin-2-yl)-3,4-dihydro-1,8-naphthyridine-1(2H)-carboxamide;

N-(4,5-dichloropyridin-2-yl)-7-formyl-3,4-dihydro-1,8-naphthyridine-1(2H)-carboxamide;

N-(5-cyanopyridin-2-yl)-7-formyl-3,4-dihydro-1,8-naphthyridine-1(2H)-carboxamide;

N-(5-chloropyridin-2-yl)-7-formyl-3,4-dihydro-1,8-naphthyridine-1(2H)-carboxamide;

7-formyl-N-(pyridin-2-yl)-3,4-dihydro-1,8-naphthyridine-1(2H)-carboxamide;

N-(4,5-dimethylpyridin-2-yl)-7-formyl-3,4-dihydro-1,8-naphthyridine-1(2H)-carboxamide;

7-formyl-N-(5-methylpyridin-2-yl)-3,4-dihydro-1,8-naphthyridine-1(2H)-carboxamide;

N-(5-cyanopyrimidin-2-yl)-7-formyl-3,4-dihydro-1,8-naphthyridine-1(2H)-carboxamide;

6-formyl-N-(5-methylpyridin-2-yl)-2H-pyrido[3,2-b][1,4]oxazine-4(3H)-carboxamide;

6-chloro-N-(5-cyanopyridin-2-yl)-7-formyl-3,4-dihydro-1,8-naphthyridine-1(2H)-carboxamide;

7-formyl-N-(6-methoxypyrimidin-4-yl)-3,4-dihydro-1,8-naphthyridine-1(2H)-carboxamide;

N-(5-cyanopyrazin-2-yl)-7-formyl-3,4-dihydro-1,8-naphthyridine-1(2H)-carboxamide;

N-(5-cyano-4-methoxypyridin-2-yl)-7-formyl-3,4-dihydro-1,8-naphthyridine-1(2H)-carboxamide;

6-formyl-N-(5-(trifluoromethyl)pyridin-2-yl)-2H-pyrido[3,2-b][1,4]oxazine-4(3H)-carboxamide;

6-fluoro-7-formyl-N-(5-(trifluoromethyl)pyridin-2-yl)-3,4-dihydro-1,8-naphthyridine-1(2H)-carboxamide;

N-(5-chloro-4-((2-(isopropylsulfonyl)phenyl)amino)pyrimidin-2-yl)-7-formyl-3,4-dihydro-1,8-naphthyridine-1(2H)-carboxamide;

N-(4,5-dicyanopyridin-2-yl)-7-formyl-3,4-dihydro-1,8-naphthyridine-1(2H)-carboxamide;

7-formyl-6-(hydroxymethyl)-N-(5-(trifluoromethyl)pyridin-2-yl)-3,4-dihydro-1,8-naphthyridine-1(2H)-carboxamide;

N-(5-cyano-4-ethoxypyridin-2-yl)-7-formyl-3,4-dihydro-1,8-naphthyridine-1(2H)-carboxamide;

7-formyl-6-methyl-N-(5-(trifluoromethyl)pyridin-2-yl)-3,4-dihydro-1,8-naphthyridine-1(2H)-carboxamide;

N-(5-cyanopyridin-2-yl)-7-formyl-6-methyl-3,4-dihydro-1,8-naphthyridine-1(2H)-carboxamide;

7-formyl-N-(5-(1-hydroxypentyl)pyridin-2-yl)-3,4-dihydro-1,8-naphthyridine-1(2H)-carboxamide;

N-(5-cyano-4-(2-methoxyethoxy)pyridin-2-yl)-7-formyl-3,4-dihydro-1,8-naphthyridine-1(2H)-carboxamide;

N-(4-chloro-5-cyanopyridin-2-yl)-7-formyl-3,4-dihydro-1,8-naphthyridine-1(2H)-carboxamide;

N-(5-cyano-4-morpholinopyridin-2-yl)-7-formyl-3,4-dihydro-1,8-naphthyridine-1(2H)-carboxamide;

N-(5-cyano-4-(4-hydroxy-4-methylpiperidin-1-yl)pyridin-2-yl)-7-formyl-3,4-dihydro-1,8-naphthyridine-1(2H)-carboxamide;

N-(5-cyanopyridin-2-yl)-7-formyl-6-(hydroxymethyl)-3,4-dihydro-1,8-naphthyridine-1(2H)-carboxamide;

N-(5-cyano-4-(2-methyl-2,8-diazaspiro[4.5]decan-8-yl)pyridin-2-yl)-7-formyl-3,4-dihydro-1,8-naphthyridine-1(2H)-carboxamide;

N-(5-cyanopyridin-2-yl)-6-cyclopropyl-7-formyl-3,4-dihydro-1,8-naphthyridine-1(2H)-carboxamide;

N-(5-cyano-4-(3,6-dihydro-2H-pyran-4-yl)pyridin-2-yl)-7-formyl-3,4-dihydro-1,8-naphthyridine-1(2H)-carboxamide;

N-(5-cyano-4-(tetrahydro-2H-pyran-4-yl)pyridin-2-yl)-7-formyl-3,4-dihydro-1,8-naphthyridine-1(2H)-carboxamide;

N-(5-chloro-4-((tetrahydrofuran-3-yl)oxy)pyrimidin-2-yl)-7-formyl-3,4-dihydro-1,8-naphthyridine-1(2H)-carboxamide;

N-(5-cyano-4-isopropoxypyridin-2-yl)-7-formyl-3,4-dihydro-1,8-naphthyridine-1(2H)-carboxamide;

N-(5-cyano-4-((tetrahydrofuran-2-yl)methoxy)pyridin-2-yl)-7-formyl-3,4-dihydro-1,8-naphthyridine-1(2H)-carboxamide;

N-(5-cyano-4-(oxetan-2-ylmethoxy)pyridin-2-yl)-7-formyl-3,4-dihydro-1,8-naphthyridine-1(2H)-carboxamide;

N-(5-cyano-4-((tetrahydro-2H-pyran-2-yl)methoxy)pyridin-2-yl)-7-formyl-3,4-dihydro-1,8-naphthyridine-1(2H)-carboxamide;

N-(5-cyanopyridin-2-yl)-6-(difluoromethyl)-7-formyl-3,4-dihydro-1,8-naphthyridine-1(2H)-carboxamide;

N-(5-cyano-4-(2-(dimethylamino)ethoxy)pyridin-2-yl)-7-formyl-3,4-dihydro-1,8-naphthyridine-1(2H)-carboxamide;

N-(5-cyano-4-(2-methoxyethoxy)pyridin-2-yl)-7-formyl-6-(hydroxymethyl)-3,4-dihydro-1,8-naphthyridine-1(2H)-carboxamide;

N-(5-cyano-4-((tetrahydrofuran-3-yl)oxy)pyridin-2-yl)-7-formyl-3,4-dihydro-1,8-naphthyridine-1(2H)-carboxamide;

N-(5-cyano-4-(4-hydroxy-4-methylpiperidin-1-yl)pyridin-2-yl)-7-formyl-6-(hydroxymethyl)-3,4-dihydro-1,8-naphthyridine-1(2H)-carboxamide;

7-acetyl-N-(5-cyanopyridin-2-yl)-6-((dimethylamino)methyl)-3,4-dihydro-1,8-naphthyridine-1(2H)-carboxamide;

N-(5-cyano-4-((tetrahydrofuran-2-yl)methoxy)pyridin-2-yl)-7-formyl-6-(hydroxymethyl)-3,4-dihydro-1,8-naphthyridine-1(2H)-carboxamide;

N-(5-cyano-4-((tetrahydro-2H-pyran-2-yl) methoxy)pyridin-2-yl)-7-formyl-6-(hydroxymethyl)-3,4-dihydro-1,8-naphthyridine-1(2H)-carboxamide;

N-(5-cyano-4-(2-methyl-2,8-diazaspiro[4.5]decan-8-yl)pyridin-2-yl)-7-formyl-6-(hydroxymethyl)-3,4-dihydro-1,8-naphthyridine-1(2H)-carboxamide;

N-(5-cyano-4-((1-methyl pyrrolidin-3-yl)oxy)pyridin-2-yl)-7-formyl-6-(hydroxymethyl)-3,4-dihydro-1,8-naphthyridine-1(2H)-carboxamide;

N-(5-cyano-4-((1-methylpiperidin-4-yl)oxy)pyridin-2-yl)-7-formyl-6-(hydroxymethyl)-3,4-dihydro-1,8-naphthyridine-1(2H)-carboxamide;

N-(5-cyano-4-((1-methoxypropan-2-yl)oxy)pyridin-2-yl)-7-formyl-6-(hydroxymethyl)-3,4-dihydro-1,8-naphthyridine-1(2H)-carboxamide;

N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide;

N-(5-cyano-4-((tetrahydrofuran-3-yl)oxy)pyridin-2-yl)-6-((dimethylamino)methyl)-7-formyl-3,4-dihydro-1,8-naphthyridine-1(2H)-carboxamide;

2-(8-((5-cyanopyridin-2-yl)carbamoyl)-2-formyl-5,6,7,8-tetrahydro-1,8-naphthyridin-3-yl)acetic acid;

N-(5-cyano-4-((tetrahydro-2H-pyran-4-yl)oxy)pyridin-2-yl)-7-formyl-6-(hydroxymethyl)-3,4-dihydro-1,8-naphthyridine-1(2H)-carboxamide;

N-(5-cyano-4-((1-methyl pyrrolidin-3-yl)oxy)pyridin-2-yl)-7-formyl-6-(hydroxymethyl)-3,4-dihydro-1,8-naphthyridine-1(2H)-carboxamide;

N-(5-cyano-4-(((tetrahydro-2H-pyran-3-yl)methyl)amino)pyridin-2-yl)-7-formyl-6-(hydroxymethyl)-3,4-dihydro-1,8-naphthyridine-1(2H)-carboxamide;

N-(5-cyano-4-((tetrahydrofuran-3-yl)amino)pyridin-2-yl)-7-formyl-6-(hydroxymethyl)-3,4-dihydro-1,8-naphthyridine-1(2H)-carboxamide;

N-(5-cyano-4-((2-methoxypropyl)amino)pyridin-2-yl)-7-formyl-6-(hydroxymethyl)-3,4-dihydro-1,8-naphthyridine-1(2H)-carboxamide;

N-(5-chloro-44(1-methoxypropan-2-yl)oxy)pyrimidin-2-yl)-7-formyl-6-(hydroxymethyl)-3,4-dihydro-1,8-naphthyridine-1(2H)-carboxamide;

N-(4-(4-chloro-2-hydroxybutoxy)-5-cyanopyridin-2-yl)-7-formyl-6-(hydroxymethyl)-3,4-dihydro-1,8-naphthyridine-1(2H)-carboxamide;

N-(5-cyano-4-(2-methoxyethoxy)pyridin-2-yl)-7-formyl-6-(trifluoromethyl)-3,4-dihydro-1,8-naphthyridine-1(2H)-carboxamide;

N-(5-cyano-4-(2-methoxyethoxy)pyridin-2-yl)-6-cyclopropyl-7-formyl-3,4-dihydro-1,8-naphthyridine-1(2H)-carboxamide;

N-(5-cyano-4-(2-methoxyethoxy)pyridin-2-yl)-6-(difluoromethyl)-7-formyl-3,4-dihydro-1,8-naphthyridine-1(2H)-carboxamide;

N-(5-cyano-4-(2-methoxyethoxy)pyridin-2-yl)-6-((dimethylamino)methyl)-7-formyl-3,4-dihydro-1,8-naphthyridine-1(2H)-carboxamide;

N-(5-cyano-4-((3-(hydroxymethyl)bicyclo[2.2.1]heptan-2-yl)amino)pyridin-2-yl)-7-formyl-6-(hydroxymethyl)-3,4-dihydro-1,8-naphthyridine-1(2H)-carboxamide;

N-(5-cyano-4-((tetrahydro-2H-pyran-4-yl)amino)pyridin-2-yl)-7-formyl-6-(hydroxymethyl)-3,4-dihydro-1,8-naphthyridine-1(2H)-carboxamide;

N-(5-cyano-4-(2-m ethoxyethoxy)pyridin-2-yl)-7-formyl-6-(methoxymethyl)-3,4-dihydro-1,8-naphthyridine-1(2H)-carboxamide;

N-(5-cyanopyridin-2-yl)-7-formyl-6-((N-methylacetamido)methyl)-3,4-dihydro-1,8-naphthyridine-1(2H)-carboxamide;

N-(5-chloro-4-((tetrahydrofuran-3-yl)oxy)pyrimidin-2-yl)-7-formyl-6-(hydroxymethyl)-3,4-dihydro-1,8-naphthyridine-1(2H)-carboxamide;

N-(5-cyano-4-((tetrahydrofuran-3-yl)oxy)pyrimidin-2-yl)-7-formyl-6-(hydroxymethyl)-3,4-dihydro-1,8-naphthyridine-1(2H)-carboxamide;

7-formyl-6-(hydroxymethyl)-N-(4-((tetrahydrofuran-3-yl)oxy)pyridin-2-yl)-3,4-dihydro-1,8-naphthyridine-1(2H)-carboxamide;

N-(5-chloro-4-((tetrahydrofuran-3-yl)oxy)pyridin-2-yl)-7-formyl-6-(hydroxymethyl)-3,4-dihydro-1,8-naphthyridine-1(2H)-carboxamide;

N-(5-cyano-4-((1-methylpiperidin-3-yl) methoxy)pyridin-2-yl)-7-formyl-6-(hydroxymethyl)-3,4-dihydro-1,8-naphthyridine-1(2H)-carboxamide;

N-(5-cyano-4-((1-methyl pyrrolidin-2-yl) methoxy)pyridin-2-yl)-7-formyl-6-(hydroxymethyl)-3,4-dihydro-1,8-naphthyridine-1(2H)-carboxamide;

N-(5-cyano-4-((1-methylpiperidin-2-yl) methoxy)pyridin-2-yl)-7-formyl-6-(hydroxymethyl)-3,4-dihydro-1,8-naphthyridine-1(2H)-carboxamide;

N-(5-fluoropyridin-2-yl)-7-formyl-6-(hydroxymethyl)-3,4-dihydro-1,8-naphthyridine-1(2H)-carboxamide;

N-(5-cyano-4-(2-(dimethylamino)ethoxy)pyridin-2-yl)-6-form-$^{13}$C-yl-2H-pyrido[3,2-b][1,4]oxazine-4(3H)-carboxamide;

N-(5-cyano-4-((1-methylpiperidin-4-yl)methoxy)pyridin-2-yl)-7-formyl-6-(hydroxymethyl)-3,4-dihydro-1,8-naphthyridine-1(2H)-carboxamide;

N-(5-cyanopyridin-2-yl)-7-formyl-4-hydroxy-3,4-dihydro-1,8-naphthyridine-1(2H)-carboxamide;

N-(5-cyano-4-((2-methoxyethyl)amino)pyridin-2-yl)-7-formyl-6-(hydroxymethyl)-3,4-dihydro-1,8-naphthyridine-1(2H)-carboxamide;

N-(5-cyano-4-(2-((dimethylamino)methyl)morpholino)pyridin-2-yl)-7-formyl-6-(hydroxymethyl)-3,4-dihydro-1,8-naphthyridine-1(2H)-carboxamide;

N-(5-cyano-4-(quinuclidin-3-yloxy)pyridin-2-yl)-7-formyl-6-(hydroxymethyl)-3,4-dihydro-1,8-naphthyridine-1 (2H)-carboxamide;

N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide;

7-formyl-6-(hydroxymethyl)-N-(44(2-methoxyethyl)amino)-5-(trifluoromethyl)pyridin-2-yl)-3,4-dihydro-1,8-naphthyridine-1(2H)-carboxamide;

N-(5-cyano-4-(4-((dimethylamino)methyl)-4-hydroxypiperidin-1-yl)pyridin-2-yl)-7-formyl-6-(hydroxymethyl)-3,4-dihydro-1,8-naphthyridine-1(2H)-carboxamide;

N-(5-cyano-4-((2-hydroxy-2-methylpropyl)amino)pyridin-2-yl)-7-formyl-6-(hydroxymethyl)-3,4-dihydro-1,8-naphthyridine-1(2H)-carboxamide;

N-(5-cyano-4-((3-(dimethylamino)-2-hydroxy-2-methylpropyl)amino)pyridin-2-yl)-7-formyl-6-(hydroxymethyl)-3,4-dihydro-1,8-naphthyridine-1(2H)-carboxamide;

N-(5-cyano-4-((2-fluoroethyl)amino)pyridin-2-yl)-7-formyl-6-(hydroxymethyl)-3,4-dihydro-1,8-naphthyridine-1(2H)-carboxamide;

N-(5-cyano-4-(2,2,2-trifluoroethoxy)pyridin-2-yl)-7-formyl-6-(hydroxymethyl)-3,4-dihydro-1,8-naphthyridine-1(2H)-carboxamide;

N-(5-cyano-4-isopropoxypyridin-2-yl)-7-formyl-6-((4-methyl-2-oxopiperazin-1-yl)methyl)-3,4-dihydro-1,8-naphthyridine-1(2H)-carboxamide;

N-(5-cyano-4-(isopropylamino)pyridin-2-yl)-7-formyl-6-((4-methyl-2-oxopiperazin-1-yl)methyl)-3,4-dihydro-1,8-naphthyridine-1(2H)-carboxamide;

N-(5-cyano-4-((2-methoxyethyl)amino)pyridin-2-yl)-7-formyl-6-((3-oxomorpholino)methyl)-3,4-dihydro-1,8-naphthyridine-1(2H)-carboxamide;

N-(5-cyano-4-((2-methoxyethyl)amino)pyridin-2-yl)-7-formyl-6-((3-hydroxy-2-oxopyrrolidin-1-yl)methyl)-3,4-dihydro-1,8-naphthyridine-1(2H)-carboxamide;

N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide;

N-(5-cyano-4-ethylpyridin-2-yl)-6,7-diformyl-3,4-dihydro-1,8-naphthyridine-1(2H)-carboxamide;

N-(5-cyano-4-((2-methoxyethyl)amino)pyridin-2-yl)-7-formyl-6-((2-oxopiperazin-1-yl)methyl)-3,4-dihydro-1,8-naphthyridine-1(2H)-carboxamide hydrochloride;

N-(5-cyano-4-((1-methoxypropan-2-yl)oxy)pyridin-2-yl)-7-formyl-6-((4-methyl-2-oxooxazolidin-3-yl)methyl)-3,4-dihydro-1,8-naphthyridine-1(2H)-carboxamide;

N-(5-cyano-4-((2-methoxyethyl)amino)pyridin-2-yl)-7-formyl-6-((3-methyl-5-oxomorpholino)methyl)-3,4-dihydro-1,8-naphthyridine-1(2H)-carboxamide;

6-((4-acetyl piperazin-1-yl)methyl)-N-(5-cyano-4-isopropoxypyridin-2-yl)-7-formyl-3,4-dihydro-1,8-naphthyridine-1(2H)-carboxamide;

N-(5-cyano-4-((2-methoxyethyl)amino)pyridin-2-yl)-7-formyl-6-(1-(N-methylacetamido)ethyl)-3,4-dihydro-1,8-naphthyridine-1(2H)-carboxamide;

N-(5-cyano-4-isopropoxypyridin-2-yl)-7-formyl-6-((2-hydroxy-N-methylacetamido)methyl)-3,4-dihydro-1,8-naphthyridine-1(2H)-carboxamide;

N-(5-cyano-4-((2-methoxyethyl)amino)pyridin-2-yl)-6-((N-(2-(dimethylamino)ethyl)acetamido)methyl)-7-formyl-3,4-dihydro-1,8-naphthyridine-1(2H)-carboxamide;

N-(5-cyano-4-((2-methoxyethyl)amino)pyridin-2-yl)-6-((N-(2-(dimethylamino)ethyl)methylsulfonamido)methyl)-7-formyl-3,4-dihydro-1,8-naphthyridine-1(2H)-carboxamide;

N-(5-cyano-4-isopropoxypyridin-2-yl)-6-((2-(dimethylamino)-N-methylacetamido)methyl)-7-formyl-3,4-dihydro-1,8-naphthyridine-1(2H)-carboxamide;

N-(5-cyano-4-((2-methoxyethyl)amino)pyridin-2-yl)-7-formyl-6-((2-methoxy-N-methylacetamido)methyl)-3,4-dihydro-1,8-naphthyridine-1(2H)-carboxamide;

N-(5-cyano-4-((2-methoxyethyl)amino)pyridin-2-yl)-7-formyl-6-((3-oxothiomorpholino)methyl)-3,4-dihydro-1,8-naphthyridine-1(2H)-carboxamide;

N-(5-cyano-4-((2-methoxyethyl)amino)pyridin-2-yl)-6-((1,1-dioxido-3-oxothiomorpholino)methyl)-7-formyl-3,4-dihydro-1,8-naphthyridine-1(2H)-carboxamide;

N-(5-cyano-4-(((4-methylmorpholin-2-yl)methyl)amino)pyridin-2-yl)-6-(difluoromethyl)-7-formyl-3,4-dihydro-1,8-naphthyridine-1(2H)-carboxamide;

N-(5-cyano-4-((1,1,1-trifluoro-3-methoxypropan-2-yl)oxy)pyridin-2-yl)-6-(difluoromethyl)-7-formyl-3,4-dihydro-1,8-naphthyridine-1(2H)-carboxamide;

N-(5-cyano-4-((2-(trifluoromethoxy)ethyl)amino)pyridin-2-yl)-7-formyl-6-((N-methylacetamido)methyl)-3,4-dihydro-1,8-naphthyridine-1(2H)-carboxamide;

6-(2-oxa-5-azaspiro[3.4]octan-5-ylmethyl)-N-(5-cyano-4-((2-methoxyethyl)amino)pyridin-2-yl)-7-formyl-3,4-dihydro-1,8-naphthyridine-1(2H)-carboxamide;

N-(4-((2-(tert-butoxy)ethyl)amino)-5-cyanopyridin-2-yl)-7-formyl-6-((4-methyl-2-oxopiperazin-1-yl)methyl)-3,4-dihydro-1,8-naphthyridine-1(2H)-carboxamide;

N-(5-cyano-4-((2-hydroxyethyl)amino)pyridin-2-yl)-7-formyl-6-((4-methyl-2-oxopiperazin-1-yl)methyl)-3,4-dihydro-1,8-naphthyridine-1(2H)-carboxamide;

N-(5-cyano-4-(2-hydroxyethoxy)pyridin-2-yl)-7-formyl-6-((4-methyl-2-oxopiperazin-1-yl)methyl)-3,4-dihydro-1,8-naphthyridine-1(2H)-carboxamide;

N-(5-cyanopyridin-2-yl)-2-formyl-7,8-dihydro-5H-pyrido[2,3-b]azepine-9(6H)-carboxamide;

N-(5-cyano-4-(2-methoxyethoxy)pyridin-2-yl)-2-formyl-7,8-dihydro-5H-pyrido[2,3-b]azepine-9(6H)-carboxamide;

N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide;

7-formyl-N-(1-isopropyl-1H-imidazo[4,5-c]pyridin-6-yl)-6-((4-methyl-2-oxopiperazin-1-yl)methyl)-3,4-dihydro-1,8-naphthyridine-1(2H)-carboxamide;

7-formyl-N-(1-isopropyl-1H-imidazo[4,5-c]pyridin-6-yl)-6-((2-oxopyrrolidin-1-yl)methyl)-3,4-dihydro-1,8-naphthyridine-1(2H)-carboxamide;

4-((8-((5-cyano-4-((2-methoxyethyl)amino)pyridin-2-yl)carbamoyl)-2-formyl-5,6,7,8-tetrahydro-1,8-naphthyridin-3-yl)methyl)-1-methyl-3-oxopiperazine 1-oxide;

N-(5-cyano-4-((2-oxopiperidin-4-yl)methoxy)pyridin-2-yl)-7-formyl-6-((2-oxopyrrolidin-1-yl)methyl)-3,4-dihydro-1,8-naphthyridine-1(2H)-carboxamide;

N-(5-cyano-4-(2-methoxyethoxy)pyridin-2-yl)-7-formyl-2-methyl-6-((4-methyl-2-oxopiperazin-1-yl)methyl)-3,4-dihydro-1,8-naphthyridine-1(2H)-carboxamide;

N-(5-cyano-4-isopropoxypyridin-2-yl)-7-formyl-2-methyl-6-((4-methyl-2-oxopiperazin-1-yl)methyl)-3,4-dihydro-1,8-naphthyridine-1(2H)-carboxamide;

N-(5-cyano-4-((2-methoxyethyl)amino)pyridin-2-yl)-7-formyl-2-methyl-6-((4-methyl-2-oxopiperazin-1-yl)methyl)-3,4-dihydro-1,8-naphthyridine-1(2H)-carboxamide;

N-(5-cyano-4-((2-methoxyethyl)amino)pyridin-2-yl)-7-formyl-6-((3-hydroxy-4-methyl-2-oxopiperazin-1-yl)methyl)-3,4-dihydro-1,8-naphthyridine-1(2H)-carboxamide;

N-(5-cyano-4-isopropoxypyridin-2-yl)-6-formyl-2,3-dihydro-1H-pyrrolo[2,3-b]pyridine-1-carboxamide;

2-((5-cyano-2-(7-formyl-6-((4-methyl-2-oxopiperazin-1-yl)methyl)-1,2,3,4-tetrahydro-1,8-naphthyridine-1-carboxamido)pyridin-4-yl)amino)ethyl hydrogen sulfate;

N-(4-(bicyclo[1.1.1]pentan-1-ylamino)-5-cyanopyridin-2-yl)-7-formyl-6-((4-methyl-2-oxopiperazin-1-yl)methyl)-3,4-dihydro-1,8-naphthyridine-1(2H)-carboxamide;

N-(5-cyano-4-(thiophen-2-ylmethoxy)pyridin-2-yl)-7-formyl-6-((N-methylacetamido)methyl)-3,4-dihydro-1,8-naphthyridine-1(2H)-carboxamide;

N-(5-cyano-4-(isopropylthio)pyridin-2-yl)-7-formyl-6-((N-methylacetamido)methyl)-3,4-dihydro-1,8-naphthyridine-1(2H)-carboxamide;

N-(5-cyano-4-((2-methoxyethyl)amino)pyridin-2-yl)-6-((3,5-dimethylpiperazin-1-yl)methyl)-7-formyl-3,4-dihydro-1,8-naphthyridine-1(2H)-carboxamide;

N-(5-cyano-4-((2-methoxyethyl)amino)pyridin-2-yl)-7-formyl-6-((3,3,4-trimethyl-2-oxopiperazin-1-yl)methyl)-3,4-dihydro-1,8-naphthyridine-1(2H)-carboxamide;

6-amino-N-(5-cyanopyridin-2-yl)-7-formyl-3,4-dihydro-1,8-naphthyridine-1(2H)-carboxamide;

N-(5-cyano-4-((2-methoxyethyl)amino)pyridin-2-yl)-7-formyl-6-(tetrahydro-2H-pyran-4-yl)-3,4-dihydro-1,8-naphthyridine-1(2H)-carboxamide;

N-(5-cyano-4-((2-methoxyethyl)amino)pyridin-2-yl)-6-(1,3-dimethyl-1H-pyrazol-4-yl)-7-formyl-3,4-dihydro-1,8-naphthyridine-1(2H)-carboxamide;

N-(5-cyano-4-((2-methoxyethyl)amino)pyridin-2-yl)-7-formyl-6-(1-methyl-1H-pyrazol-4-yl)-3,4-dihydro-1,8-naphthyridine-1(2H)-carboxamide;

N-(5-cyano-4-((2-methoxyethyl)amino)pyridin-2-yl)-7-formyl-6-(2-methylthiazol-5-yl)-3,4-dihydro-1,8-naphthyridine-1(2H)-carboxamide;

N-(5-cyano-4-((2-methoxyethyl)amino)pyridin-2-yl)-7-formyl-6-(thiophen-2-yl)-3,4-dihydro-1,8-naphthyridine-1(2H)-carboxamide;

N-(5-cyano-4-((2-methoxyethyl)amino)pyridin-2-yl)-7-formyl-6-(1H-imidazol-1-yl)-3,4-dihydro-1,8-naphthyridine-1(2H)-carboxamide;

N-(5-cyano-4-((2-methoxyethyl)amino)pyridin-2-yl)-7-formyl-6-(pyridin-3-yl)-3,4-dihydro-1,8-naphthyridine-1(2H)-carboxamide;

N-(5-cyano-4-((2-methoxyethyl)amino)pyridin-2-yl)-7-formyl-6-(1-methyl-1H-pyrazol-5-yl)-3,4-dihydro-1,8-naphthyridine-1(2H)-carboxamide;

N-(5-cyano-4-((2-methoxyethyl)amino)pyridin-2-yl)-7-formyl-6-(3-methyl-1H-1,2,4-triazol-1-yl)-3,4-dihydro-1,8-naphthyridine-1(2H)-carboxamide;

N-(5-cyano-4-((2-methoxyethyl)amino)pyridin-2-yl)-7-formyl-6-(3-methyl-2-oxopyrrolidin-1-yl)-3,4-dihydro-1,8-naphthyridine-1(2H)-carboxamide;

N-(5-cyano-4-((2-methoxyethyl)amino)pyridin-2-yl)-7-formyl-6-(3-oxomorpholino)-3,4-dihydro-1,8-naphthyridine-1(2H)-carboxamide;

N-(5-cyano-4-((2-methoxyethyl)amino)pyridin-2-yl)-7-formyl-6-(2-oxooxazolidin-3-yl)-3,4-dihydro-1,8-naphthyridine-1(2H)-carboxamide;

N-(5-cyano-4-isopropoxypyridin-2-yl)-7-formyl-6-(tetrahydrofuran-3-yl)-3,4-dihydro-1,8-naphthyridine-1(2H)-carboxamide;

N-(5-cyano-4-isopropoxypyridin-2-yl)-7-formyl-6-(piperidin-4-yl)-3,4-dihydro-1,8-naphthyridine-1(2H)-carboxamide;

N-(5-cyano-4-((2-methoxyethyl)amino)pyridin-2-yl)-7-formyl-6-(1-(oxetan-3-yl)piperidin-4-yl)-3,4-dihydro-1,8-naphthyridine-1(2H)-carboxamide; and N-(5-cyano-4-((2-methoxyethyl)amino)pyridin-2-yl)-6-(1-(2,2-difluoroethyl)piperidin-4-yl)-7-formyl-3,4-dihydro-1,8-naphthyridine-1(2H)-carboxamide in free form or in pharmaceutically acceptable salt form.

Embodiment 24

A pharmaceutical combination for use according to embodiment 22 or 23, wherein the FGFR4 inhibitor is N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form.

Embodiment 25

A pharmaceutical combination for use according to any of embodiments 22 to 24, wherein the FGFR4 inhibitor is N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form.

Embodiment 26

A pharmaceutical combination for use according to any of embodiments 19 to 25, wherein the side effect is elevated liver enzymes.

Embodiment 27

A pharmaceutical combination for use according to any of embodiments 19 to 26, wherein the side effect is elevated ALT.

Embodiment 28

A pharmaceutical combination for use according to any of embodiments 19 to 26, wherein the side effect is elevated AST.

Embodiment 29

A pharmaceutical combination for use according to any of embodiments 19 to 25, wherein the side effect is elevated miRNA122.

Embodiment 30

A pharmaceutical combination for use according to any of embodiments 19 to 29, wherein the FGFR4 inhibition therapy is for the treatment of cancer.

Embodiment 31

A pharmaceutical combination for use according to any of embodiments 19 to 30, wherein the FGFR4 inhibition therapy is for the treatment of liver cancer, breast cancer, glioblastoma, prostate cancer, rhabdomyosarcoma, gastric cancer, ovarian cancer, lung cancer, colon cancer.

Embodiment 32

A pharmaceutical combination for use according to embodiment 30, wherein the FGFR4 inhibition therapy is for the treatment of liver cancer.

Embodiment 33

A pharmaceutical combination comprising an FGFR4 inhibitor and a bile acid sequestrant for use in a therapeutic regimen comprising the simultaneous or sequential administration of said FGFR4 inhibitor and a bile acid sequestrant.

Embodiment 34

A pharmaceutical combination for use according to embodiment 33, wherein the FGFR4 inhibitor is N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form and the bile acid sequestrant is cholestyramine.

Embodiment 35

A pharmaceutical combination for use according to embodiment 33 or 34 wherein the therapeutic regimen is for the treatment of liver cancer.

The following example is intended to illustrate the invention and is not to be construed as being limitations thereon.

EXAMPLES

Example 1

N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide was synthesized as described in WO2015059668, example 83.

N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (Compound A (Cpd A)) and cholestyramine (CHO) (also known as Questran Powder [Cholestyramine for Oral Suspension, USP]; NDC no.: 49884-09366-66; lot no.: 26079601) were each administered as a formulation in their respective vehicles [For compound A: 100 mM Citrate buffer, pH 2.5; for cholestyramine:water].

Male Beagle dogs were obtained from Marshall BioResources (North Rose, N.Y.). For the study, all animals were nave to treatment. All animals used in the study were healthy and suitable for use. The dose volume for Cpd A and its vehicle was 5 mL/kg. For CHO, the dosing aliquot was dispersed in 75 mL total animal drinking water.

For the study, a dosing paradigm was followed with initial loading dose of either vehicle or CHO on the last day of pretest (day −1), and dosing of either vehicle or CHO on days 1-7.

TABLE 1

Animal allocation and test article doses for the study phase

| Group | Number | Dose/Conc. water | Dose* CHO | Dose Cpd A (mg/kg/day) | Conc. (mg/mL) |
|---|---|---|---|---|---|
| Group 1 | 6 | 0 | | 5 | 1 |
| Group 2 | 6 | | 5/11.25 | 5 | 1 |

*Cholestyramine (CHO) amount to be given was approximately 5 grams/dosing event; 11.25 grams of Questran powder contained 5 grams of Cholestyramine resin, USP.

N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide dosing was initiated on day 8, with the second dosing event of each day for either vehicle or CHO. Food was presented to the animals after the second daily dosing event. Animals were not dosed on day 15. Dosing was restarted on day 24 and the dose groups crossed over on day 38-44, with the last day of dosing on day 44.

Clinical observations, twice-weekly body weights, and daily food consumption determinations were performed.

Fecal samples were collected for bile acid (BA) analysis once during pretest and on days 7, 10, 14, 17, 24, 28, 35, 42, and 49.

Plasma was collected from all animals for bile acid profiling during the study, concurrent with clinical pathology and/or toxicokinetic sampling as follows: at approximately 3 hours postdose (post vehicle, CHO or Cpd A, as appropriate) on days 1, 3, 7, 8, 11, 14, 15, 18, 21, 23, 25, 28, 31, 35, 38, 42, 45, 49, and 52. On days 8, 14, 25, and 39 only, samples were collected at predose and approximately 0.5, 1, 3, 7, and 24 hours postdose (post Cpd A dosing). In addition, on day 44, bile acid biomarker samples were collected at 3, 7, and 24 hours postdose (concurrent with the last toxicokinetic blood collection).

With regards to serum ALT activity: In general, minimal to moderate increases in serum ALT activity were associated with the administration of Compound A, which were ameliorated by the co-administration of cholestyramine. These changes are illustrated in FIG. 1.

Co-administration with cholestyramine, with resultant intestinal bile acid sequestration, thus decreases intrahepatic bile acid accumulation thus mitigating the Compound A-related ALT activity increases.

When compared with pretest results, the administration of Compound A alone (Group 1) resulted in minimal to modest increases in serum ALT activity 3.5 fold). In contrast to this, animals in Group 2 (dosed with Compound A co-administered with cholestyramine) showed no relevant changes in serum ALT activity over this same time period.

Following the first cross-over, the administration of Compound A with cholestyramine (Group 1) showed no changes in serum ALT activity over this dosing period. However, in Group 2 (Compound A alone) serum ALT activity increases were minimal to moderate 6 fold) over this time period. In contrast to this, animals in Group 2 (dosed with Compound A co-administered with cholestyramine) showed no changes in serum ALT activity over this same time period.

Following the second cross-over, the administration of Compound A alone (Group 1) resulted in minimal to modest increases in serum ALT activity 3.5 fold). In contrast to this, animals in Group 2 (dosed with Compound A co-administered with cholestyramine) showed return of ALT activity towards pretest.

These findings indicate that a combination of an FGFR4 inhibitor and a bile acid sequestrant could be useful in reducing or mitigating side-effects associated with FGFR4 inhibition therapy, e.g associated with the administration of Compound A, or a pharmaceutically acceptable salt thereof.

Example 2

Plasma miR-122 levels, a liver enriched microRNA used as biomarker of liver injury (Starkey Lewis P J et al., Clin Pharmacol Ther, 2012, 291-293), were determined. miR-122 is considered as a liver-specific marker.

Material and Methods

Small RNA Extraction from Plasma

Small RNA was extracted from 50 µl of plasma by using the miRNeasy/MinElute kit and following the instructions of the manufacturer (Qiagen). Elution of small RNA was realized in 14 µl of nucleic acid-free $H_2O$.

Reverse Transcription and Preamplification 3.2 µl of eluted small RNA was reverse transcribed into cDNA by using the Megaplex RT primer human pool A and B and the Taqman MicorRNA Reverse Transcription kit (Applied Biosystems/Life Technologies, reference 4366596) and following the instructions of the manufacturer.

2.5 µl of cDNA was preamplified by using the Megaplex Preamp primer human pool A and B (Applied Biosystems/Life Technologies, reference 4399201 and 4399233) and the Taqman PreAmp Master mix (Applied Biosystems/Life Technologies, reference 4391128) and following the instructions of the manufacturer.

Amplification of miR-122 microRNA miR-122 was amplified from preamplified cDNA by using a commercially available validated Taqman assay (reference 002245) diluted in the Taqman MasterMixII (Applied Biosystems/Life Technologies) and following the instructions of the manufacturer.

The relative quantification of plasmatic microRNA levels was performed using the standard curve method to generate expression values as number of molecules.

Statistical Analysis

Statistical significance of mRNA measurements was assessed using the two-sample unequal variance, two-tailed distribution (hetero-scedastic Student's t-test, Excel). Coefficients of variation with a P value <0.05 were considered to be statistically significant.

Study Days 1-7: Group 1: Vehicle; Group 2: Cholestyramine

Treatments with vehicle and CHO did not affect miR-122 levels.

Study Day 8-14: Group 1: Vehicle+ Cpd A; Group 2: CHO+ Cpd A

When compared with Study day 1-7 results, the administration of Cpd A with vehicle alone (Group 1) and the administration of CHO with Cpd A (Group 2) resulted in incidental and non-relevant increases in miR-122 levels (maximum average, Group 1≤2.5 fold at day 14; Group 2≤11.6 fold at day 14).

Study Day 15-23: Group 1 and 2: Recovery

When compared with Study day 1-7 results, the recovery period resulted in incidental and biologically non-significant increases in miR-122 levels (maximum average, Group 1≤5.4 fold at day 21; Group 2≤11.7 fold at day 21).

Study Days 25-38: Group 1: Cpd A+Cholestyramine; Group 2: Cpd A+Vehicle

When compared with Study day 1-7 results, the administration of CHO with Cpd A (Group 1) resulted in incidental and biologically non-significant increases in miR-122 levels (maximum average, Group 1≤5.8 fold at day 35). The administration of Cpd A with vehicle alone (Group 2) resulted in a significant and time-dependent increase in miR-122 levels in the animal 2003 (maximum: ≤151 fold at day 38). The treatment also induced a significant increase in miR-122 levels in animal 2006 (maximum average at day 31: ≤63 fold).

Study Days 39-42: Group 1: Cpd A Vehicle; Group 2: Cpd A+Cholestyramine

Following the second cross-over, the administration of Cpd A with vehicle alone (Group 1) resulted in incidental and minimal increases in miR-122 levels (average. ≤7.8 fold). In contrast to this, animals in Group 2 (dosed with Cpd A co-administered with cholestyramine) showed return of miR-122 levels towards controls.

Study Days 45-52: Group 1 and 2: Recovery

When compared with Study day 1-7 results, the recovery period resulted in significant and transient increases in miR-122 levels in 2 animals from Group 1 (peak at day 49: animal 1003: ≤47.9 fold; animal 1006: ≤40.1 fold). Similarly, transient and minimal increases of miR-122 levels were observed in 2 others animals from Group 1 (peak at day 49: animal 1001: ≤22.2 fold; animal 1005: ≤16.4 fold). In Group 2, miR-122 levels in animal 2003 showed a moderate but time-dependent increase (day 45: ≤12 fold; day 49≤39 fold; day 52≤89 fold). Similarly, transient and minimal increases of miR-122 levels were observed in 2 others animals from Group 2 (Day 52: animal 2001: ≤42 fold; animal 2006: ≤43 fold).

Some animals treated with compound A showed minimal to moderate increases in miR122 compared to respective controls, which after co-treatment with CHO followed a trend towards decreased miR-122 level.

These data suggest that cholestyramine can be used simultaneously or sequentially to an FGFR4 inhibitor and thereby reduce side-effects associated with FGFR4 inhibition therapy.

What is claimed:

1. A method of reducing side effects associated with FGFR4 inhibitor therapy, wherein the side effects comprise the increase of
   (a) liver enzyme in the serum, plasma or blood of the subject taking FGFR4 inhibition therapy, wherein the liver enzyme comprises alanine aminotransferase, or
   (b) miRNA122 in the subject taking FGFR4 inhibition therapy,
   wherein the FGFR4 inhibition therapy is for the treatment of liver cancer and the FGFR4 inhibition therapy comprises administration of an FGFR4 inhibitor which comprises N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide;

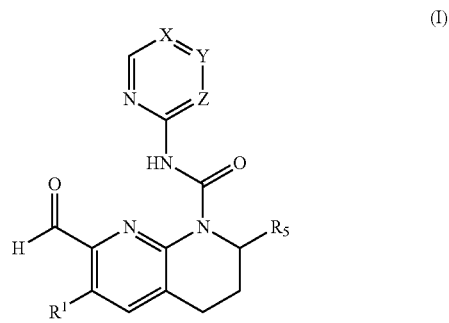

(I)

and
a bile acid sequestrant.

2. A pharmaceutical combination for the treatment of liver cancer comprising N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and a bile acid sequestrant.

3. The pharmaceutical combination according to claim 2, wherein the FGFR4 inhibitor is N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form.

4. The method of claim 1, wherein the bile acid sequestrant is selected from cholestyramine, colesevelam, colesevalam hydrochloride, colestipol or selevamer.

5. The pharmaceutical combination according to claim 2, wherein the bile acid sequestrant is cholestyramine.

6. The method of claim 1, wherein the side effects associated with FGFR4 inhibition therapy are side effects associated with treatment of liver cancer, wherein the FGFR4 inhibitor is N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form, and wherein the side effects associated with treatment of liver cancer do not include diarrhea.

7. The method of claim 1, wherein the bile acid sequestrant is cholestyramine.

8. A method for reducing side effects associated with FGFR4 inhibition therapy in a subject, the method comprising simultaneously or sequentially administering to the subject cholestyramine and an FGFR4 inhibitor comprising N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form.

9. The method of claim 8, wherein the FGFR4 inhibition therapy is for the treatment of liver cancer.

10. A method for reducing side effects associated with FGFR4 inhibition therapy in a subject afflicted with liver cancer, the method comprising simultaneously or sequentially administering to the subject an FGFR4 inhibitor for the treatment of liver cancer and a bile acid sequestrant, wherein the side effects comprise the increase of
   (a) liver enzymes in the serum, plasma or blood of the subject taking FGFR4 inhibition therapy, wherein the liver enzyme compromises alanine aminotransferase, or
   (b) miRNA122 in the subject taking FGFR4 inhibition therapy,
   wherein the FGFR4 inhibitor is N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form, in pharmaceutically acceptable salt form or in citric acid form.

11. The method of claim 10, wherein the bile acid sequestrant is cholestyramine.

12. The method of claim 10, wherein the bile acid sequestrant is selected from cholestyramine, colesevelam, colesevalam hydrochloride, colestipol or selevamer.

* * * * *